(12) United States Patent
Mace

(10) Patent No.: US 7,510,564 B2
(45) Date of Patent: Mar. 31, 2009

(54) LANCING DEVICE

(75) Inventor: Chad Harold Mace, Hudson, NH (US)

(73) Assignee: Abbott Diabetes Care Inc., Alameda, CA (US)

( * ) Notice: Subject to any disclaimer, the term of this patent is extended or adjusted under 35 U.S.C. 154(b) by 989 days.

(21) Appl. No.: 10/607,957

(22) Filed: Jun. 27, 2003

(65) Prior Publication Data

US 2004/0267300 A1 Dec. 30, 2004

(51) Int. Cl.
*A61B 17/32* (2006.01)
(52) U.S. Cl. ..................................... 606/181
(58) Field of Classification Search ........................ None
See application file for complete search history.

(56) References Cited

U.S. PATENT DOCUMENTS

| | | | |
|---|---|---|---|
| 4,462,405 A | | 7/1984 | Ehrlich |
| 4,503,856 A | | 3/1985 | Cornell et al. |
| RE32,922 E | | 5/1989 | Levin et al. |
| 4,840,457 A | * | 6/1989 | Remer ......................... 359/824 |
| 5,201,324 A | | 4/1993 | Swierczek |
| 5,318,583 A | * | 6/1994 | Rabenau et al. ............. 606/182 |
| 5,318,584 A | | 6/1994 | Lange et al. |
| 5,361,243 A | * | 11/1994 | Kasahara .................. 369/44.15 |
| 5,476,474 A | * | 12/1995 | Davis et al. .................. 606/182 |
| 5,514,152 A | * | 5/1996 | Smith ............................ 606/182 |
| 5,540,709 A | | 7/1996 | Ramel |
| 5,613,978 A | | 3/1997 | Harding |
| 5,645,555 A | * | 7/1997 | Davis et al. .................. 606/182 |
| 5,709,699 A | | 1/1998 | Warner |
| RE35,803 E | | 5/1998 | Lange et al. |
| 5,755,733 A | | 5/1998 | Morita |
| 5,951,582 A | * | 9/1999 | Thorne et al. ................ 606/182 |
| 5,984,940 A | | 11/1999 | Davis et al. |
| 6,109,227 A | * | 8/2000 | Mott ........................ 123/90.31 |
| 6,322,574 B1 | | 11/2001 | Lloyd et al. |
| 6,358,265 B1 | | 3/2002 | Thorne, Jr. et al. |
| 6,409,740 B1 | | 6/2002 | Kuhr et al. |
| 6,419,661 B1 | | 7/2002 | Kuhr et al. |

(Continued)

*Primary Examiner*—Todd E Manahan
*Assistant Examiner*—Tuan V Nguyen
(74) *Attorney, Agent, or Firm*—Edward J. Baba; Bozicevic, Field & Francis LLP

(57) ABSTRACT

A lancing device is adapted for use in firing a lancet into the skin of a patient to acquire a blood sample and, subsequent thereto, calculating and displaying the concentration of glucose in the acquired sample. In one embodiment, the device comprises a lancet and a torsion spring coupled to the lancet through a lancet holder. The torsion spring includes inner, middle and outer rings which are concentrically configured, a plurality of activation spring arms which connect the middle and outer rings and a plurality of return spring arms which connect the inner and middle rings. In use, the plurality of activation and return spring arms can be independently transformed between energized and de-energized states using a single, button-shaped mechanism. Rotation of the mechanism is used to energize the activation and return spring arms. With the return spring arms maintained in their energized state, depression of the mechanism transforms the activation spring arms from their energized state to their de-energized state which drives the lancet from a retracted position to an extended position. Once the activation spring arms reach their de-energized state, the return spring arms transform from their energized state to their de-energized state which pulls the lancet back from its extended position to its retracted position.

39 Claims, 16 Drawing Sheets

U.S. PATENT DOCUMENTS

| | | | |
|---|---|---|---|
| 7,223,276 B2 * | 5/2007 | List et al. | 606/181 |
| 7,273,484 B2 * | 9/2007 | Thoes et al. | 606/181 |
| 2001/0010109 A1 * | 8/2001 | Jager | 16/199 |
| 2001/0027326 A1 | 10/2001 | Schraga | |
| 2002/0087180 A1 | 7/2002 | Searle et al. | |

* cited by examiner

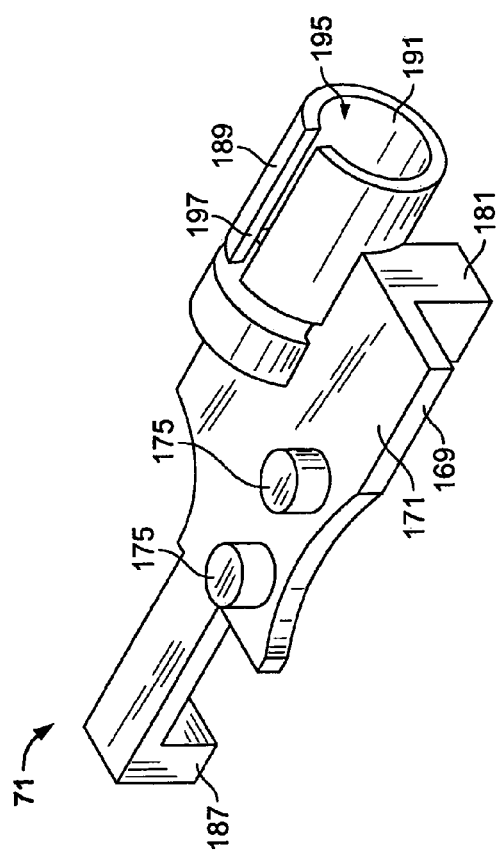
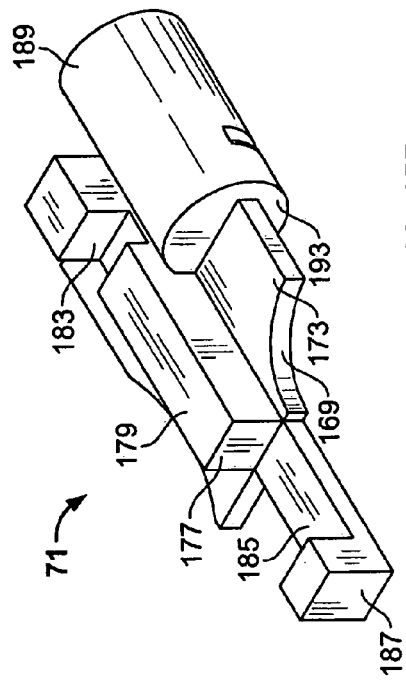
FIG. 15A
FIG. 15B

LANCING DEVICE

BACKGROUND OF THE INVENTION

The present invention relates generally to lancing devices and more particularly to a novel lancing device.

Diabetes is a disease which typically requires a patient to routinely measure the concentration of glucose in his/her blood. Based upon the results of each blood glucose measurement, the patient may require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A two-step process is commonly practiced by diabetes patients to self-monitor the level of glucose present in their blood. In the first step, the patient pricks his/her finger in order to acquire a small sample of blood. In the second step, a blood glucose monitor is used to calculate and, in turn, digitally display the concentration of glucose present in the blood sample.

Blood samples taken from a patient for blood glucose monitoring are typically obtained by piercing the skin of the patient using a lancet device (also referred to herein as a lancing device). A lancet device typically includes a body and a lancet. The body is typically adapted to be held by the user, the lancet being coupled to the body and being adapted to pierce the skin of the patient so as to draw blood therefrom. In some lancet devices, the lancet extends from the body at all times. As can readily be appreciated, such lancet devices may inadvertently prick people and/or become contaminated with foreign objects and, therefore, pose a safety risk. Accordingly, in other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position in order to minimize the risk of inadvertent lancet sticks.

Lancet devices having a movable lancet typically fall into one of two types: single-use lancet devices or multi-use lancet devices.

In single-use, or pre-loaded, lancet devices, the lancet is, prior to use and without any prepping by a user, maintained in an armed state, ready to be fired. The firing of a lancet in such a device is typically effected either by pressing or compressing the entire device against the skin of the patient or by depressing a movable plunger or trigger on the device while holding the remainder of the device against the skin of the patient. Examples of the aforementioned type of lancet device are disclosed in the following documents, all of which are incorporated herein by reference: U.S. Pat. No. 5,201,324, inventor Swierczek, issued Apr. 13, 1993; U.S. Pat. No. 5,540,709, inventor Ramel, issued Jul. 30, 1996; U.S. Pat. No. 5,709,699, inventor Warner, issued Jan. 20, 1998; U.S. Pat. No. 5,755,733, inventor Morita, issued May 26, 1998; U.S. Pat. No. 6,322,574, inventors Lloyd et al., issued Nov. 27, 2001; U.S. Pat. No. 6,358,265, inventors Thorne, Jr. et al., issued Mar. 19, 2002; and U.S. patent application Publication No. US 2002/0087180, inventors Searle et al., published Jul. 4, 2002.

One drawback associated with single-use lancet devices is that it is possible for the lancet to be fired prematurely simply by the inadvertent application of pressure to the lancet device. As can readily be appreciated, the premature firing of the lancet may result in an undesired piercing of a person and/or in the contamination of the lancet. In addition, the premature firing of the lancet will prevent the lancet device from later being used for its intended purpose.

In multi-use lancet devices, the lancet device typically takes the form of a pen-shaped device comprising a spring-loaded lancet, cocking means for storing energy in the spring, and trigger means for releasing the energy stored in the spring to drive movement of the lancet. In use, the spring is cocked, the device is held against the skin of the patient, and the trigger is fired. Examples of the aforementioned type of lancet device are disclosed in the following documents, all of which are incorporated herein by reference: U.S. Pat. No. 4,462,405, inventor Ehrlich, issued Jul. 31, 1984; U.S. Pat. No. 4,503,856, inventor Cornell et al., issued Mar. 12, 1985; U.S. Reissue Pat. No. 32,922, inventors Levin et al., reissued May 16, 1989; U.S. Pat. No. 5,613,978, inventor Harding, issued Mar. 25, 1997; and U.S. patent application Publication No. US 2001/0027326, inventor Schraga, published Oct. 4, 2001.

Of the above documents, U.S. Reissue Pat. No. 32,922 is illustrative. In this patent, there is disclosed a lancet device comprising an inner tubular member and an outer tubular member, the inner tubular member being telescopically mounted within the outer tubular member. A lancet holder is slidably mounted within the inner tubular member, the lancet holder removably receiving at its forward end a lancet. A shaft extends rearwardly from the lancet holder, the shaft traveling through the inner tubular member and terminating within the outer tubular member. A first linear spring is mounted on the shaft within the inner tubular member, the first linear spring biasing the lancet holder forward. A finger formed on the lancet holder is adapted to extend radially outward through a transverse opening in the inner tubular member. A trigger mounted externally to the inner tubular member is adapted to engage the lancet holder finger and to push said finger into the inner tubular member through the transverse opening. To store energy into the device for subsequent firing, the outer tubular member is pulled away from the inner tubular member and then released. The pulling away of the outer tubular member causes the shaft to be pulled rearwardly and the first linear spring to be compressed. In addition, the pulling away of the outer tubular member causes the finger on the lancet holder to be drawn into the transverse opening in the inner tubular member, thereby retaining the first linear spring in its compressed state. To fire the device, the trigger is depressed. Depression of the trigger causes the finger to be pushed back into the inner tubular member, thereby releasing the first linear spring. The release of the first linear spring results in the lancet being driven forward, out through the end of the inner tubular member, and into the finger of the patient. After firing, a second linear spring, which is located in the outer, tubular member surrounding the rear end of the shaft, draws the lancet back into the inner tubular member in order to minimize the risk of inadvertent contact with the used lancet.

One drawback associated with the aforementioned lancet device is that such a lancet device typically comprises a pair of linear springs, one of which is used to fire the lancet out from the protective body and into the skin of the patient and another which is used to retract the lancet back into the body after pricking the skin of the patient. As can be appreciated, the inclusion of a pair of linear springs significantly increases the overall length of the lancet device. Accordingly, it has been found by lancet design engineers to be difficult to contain such a device into a relatively compact package, which is highly desirable.

Accordingly, in U.S. Pat. No. 5,645,555 to R. M. Davis et al., which is incorporated herein by reference, a lancet device is provided which uses a single torsion spring to both fire and retract a lancet blade. Specifically, the lancet device includes a housing having an opening for operating projection of a lancet blade. An actuator mechanism includes a drive spring structure insertably mounted in the housing and arranged to drive pivotal motion of the lancet blade including sequential thrusting of the blade from the housing aperture followed by immediate pivotally reverse retracting of the blade from the aperture into the housing as the spring de-energizes.

The particular construction of the aforementioned lancet device provides it with a notable advantage over other types of conventional lancet devices. Specifically, because the lancet device utilizes a single torsion spring to both fire and retract the lancet blade, the lancet device is capable of being packaged into a relatively compact housing, which is highly desirable.

However, it is also to be understood that the aforementioned device suffers from a few notable drawbacks.

As a first drawback, the aforementioned lancing device is of the pre-loaded variety, with the torsion spring originally configured in its pre-stressed, or cocked, state. As a result, the lancet device is incapable of more than a single use, which is highly undesirable.

As a second drawback, the aforementioned lancing device is designed to cleave, and not prick, the skin of a patient. As can be appreciated, the cleaving process creates a relatively large incision in the skin of a patient. The large incision created through the cleaving process can result in excessive patient bleeding and pain, which is highly undesirable.

SUMMARY OF THE INVENTION

It is an object of the present invention to provide a novel lancet device.

It is another object of the present invention to provide a novel lancing device which can be used on more than one occasion.

It is yet another object of the present invention to provide a lancing device of the type as described above is relatively compact in construction.

It is yet still another object of the present invention to provide a lancing device of the type described above which has a limited number of parts, which is inexpensive to manufacture and which is easy to use.

Therefore, according to one feature of the present invention, there is provided a lancing device comprising a lancet, said lancet having a sharpened tip, and a torsion spring coupled to said lancet, said torsion spring comprising first and second concentric rings which are connected by a spring arm.

According to another feature of the present invention, there is provided a lancing device comprising a lancet, said lancet having a sharpened tip, and a torsion spring coupled to said lancet, said torsion spring comprising, an inner ring, a middle ring concentrically configured around said inner ring, an outer ring concentrically configured around said middle ring, a first spring arm connecting said middle ring to said outer ring, and a second spring arm connecting said inner ring to said middle ring.

According to another feature of the present invention, there is provided a lancing device comprising a lancet, said lancet having a sharpened tip, a torsion spring coupled to said lancet, said torsion spring comprising a spring arm which is transformable between an energized state and a de-energized state, and a mechanism coupled to said torsion spring, wherein transformation of the spring arm of said torsion spring from its de-energized state to its energized state is effected through the manual activation of said mechanism.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIGS. 15(a) and (b) are enlarged front and rear perspective views, respectively, of the lancet holder shown in FIG. 3;

DETAILED DESCRIPTION OF THE PREFERRED EMBODIMENT

Figure 1:
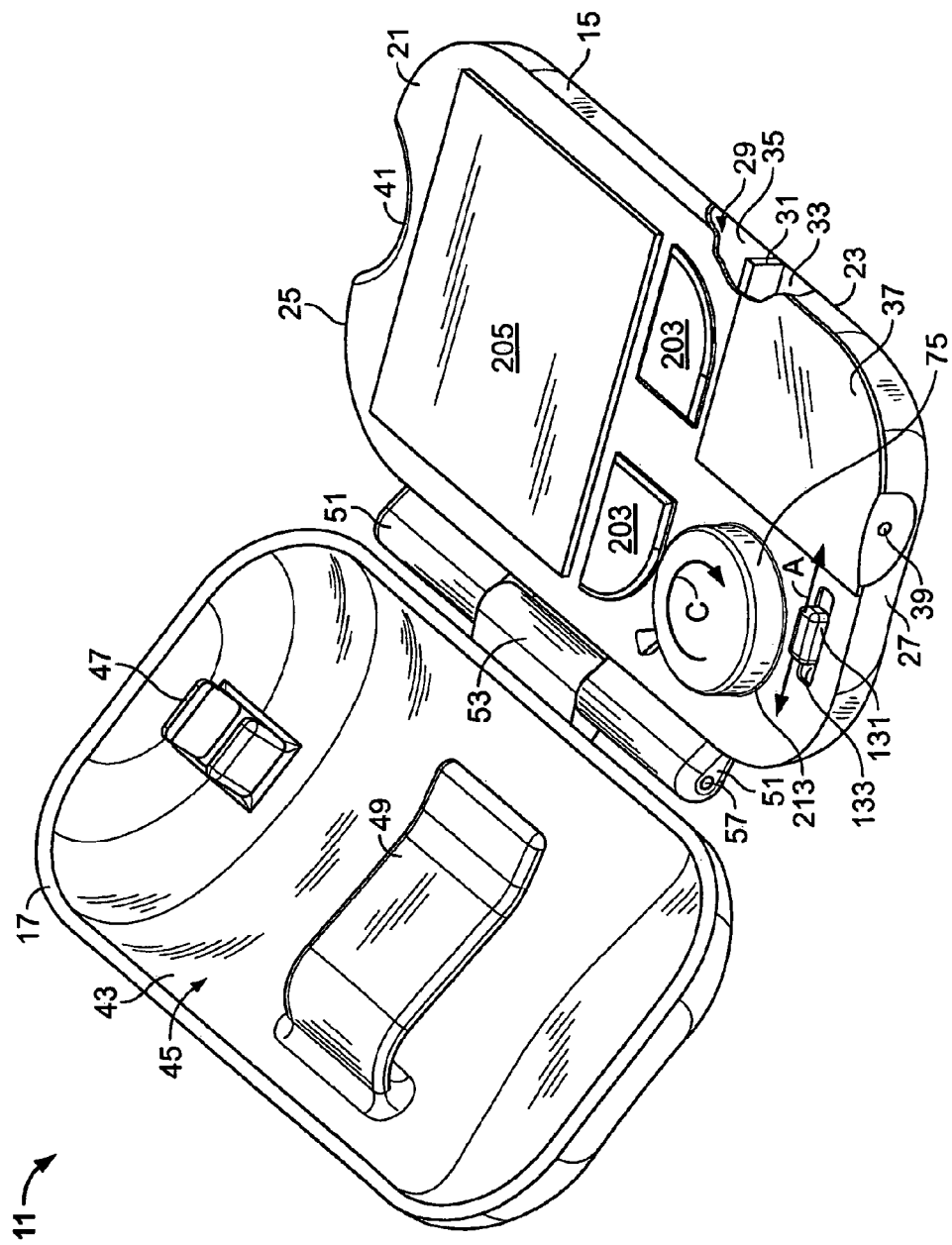
FIG. 1 is a front perspective view of a first embodiment of a lancing device constructed according to the teachings of the present invention, the lancing device being shown with its cover disposed in its open position.
Figure 2:
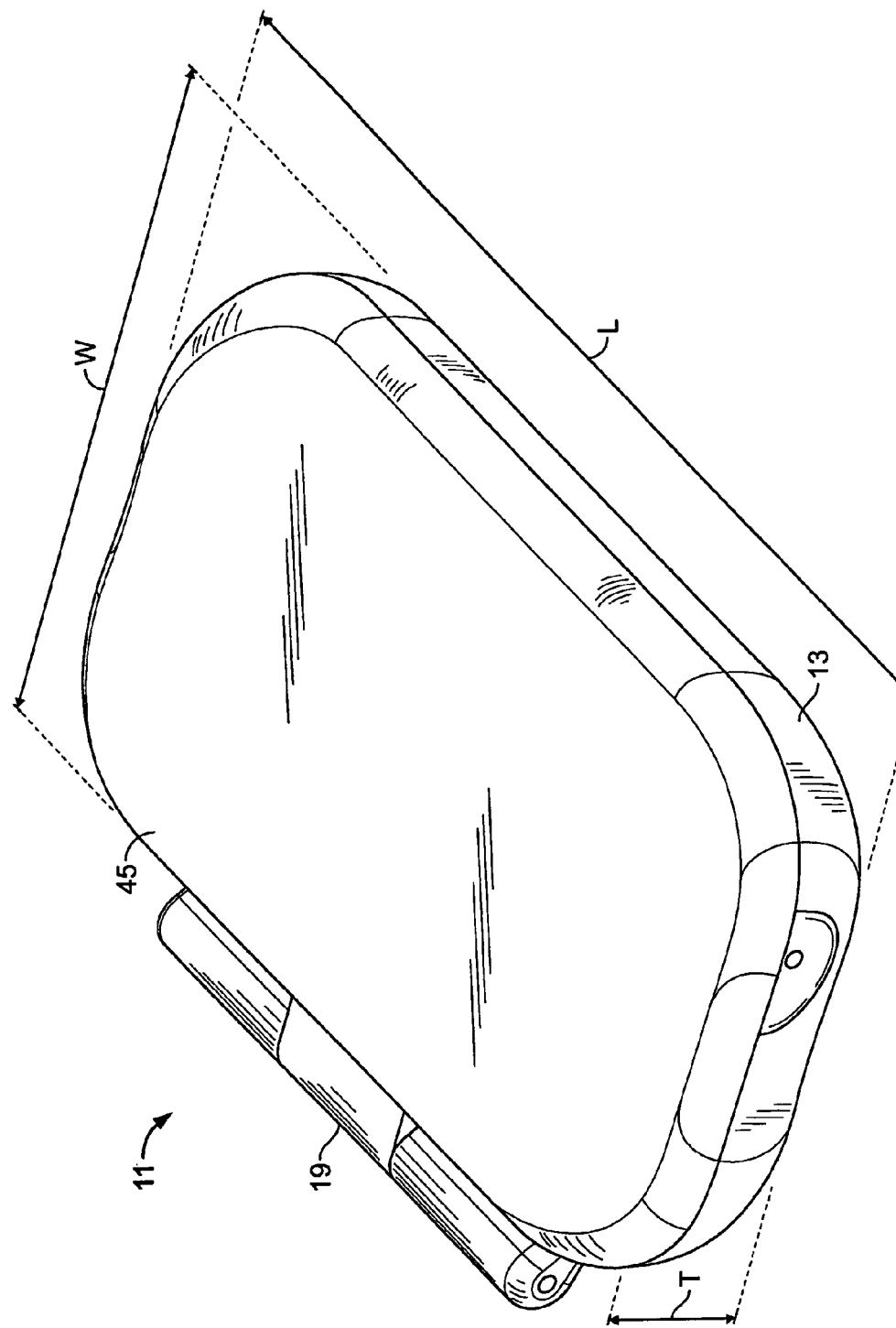
FIG. 2 is a front perspective view of the lancing device shown in FIG. 1, the lancing device being shown with its cover disposed in its closed position.
Figure 3:
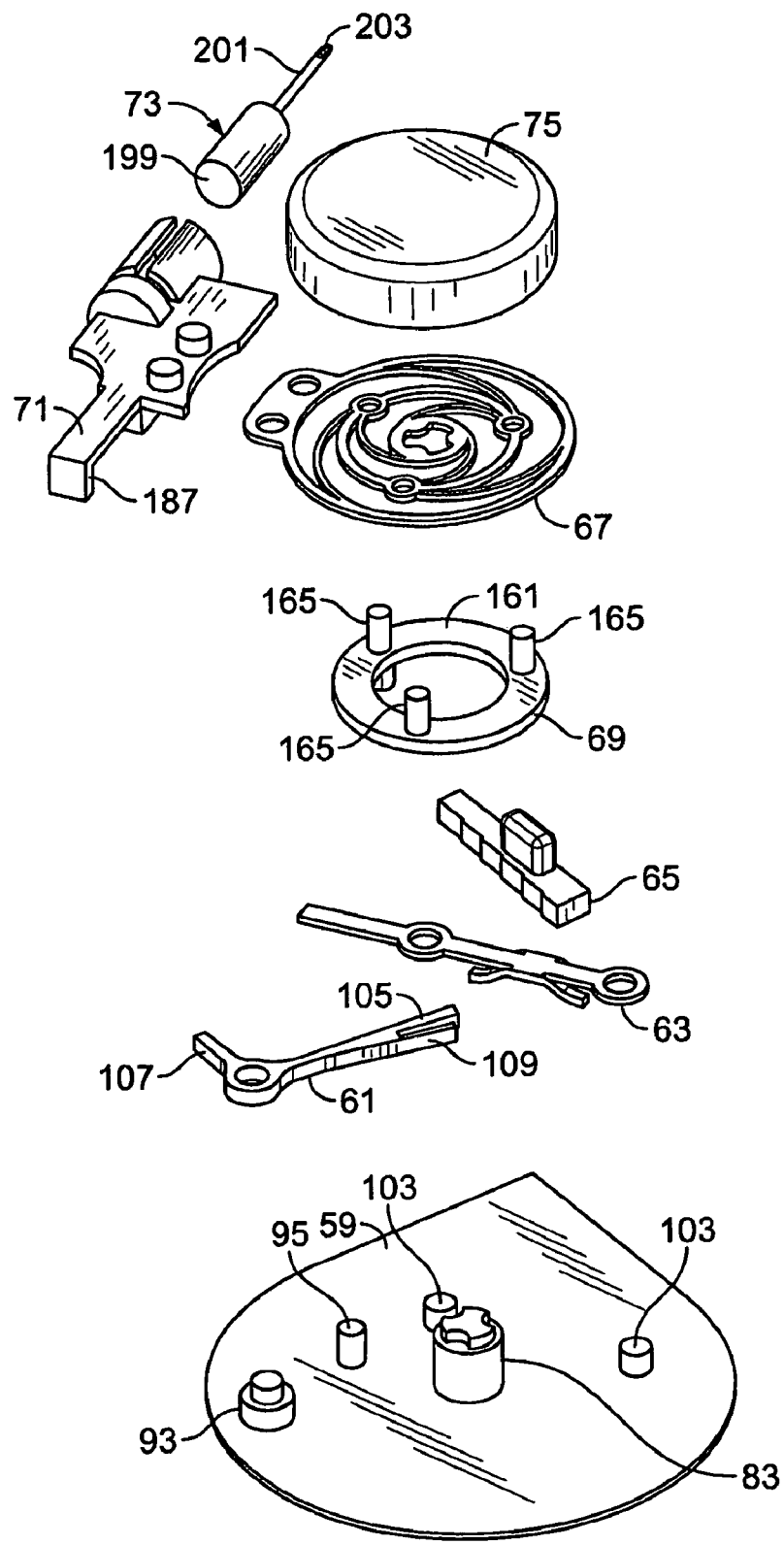
FIG. 3 is a top, front, exploded perspective view of selected internal components disposed within the first compartment of the housing shown in FIG. 1.
Figure 4:
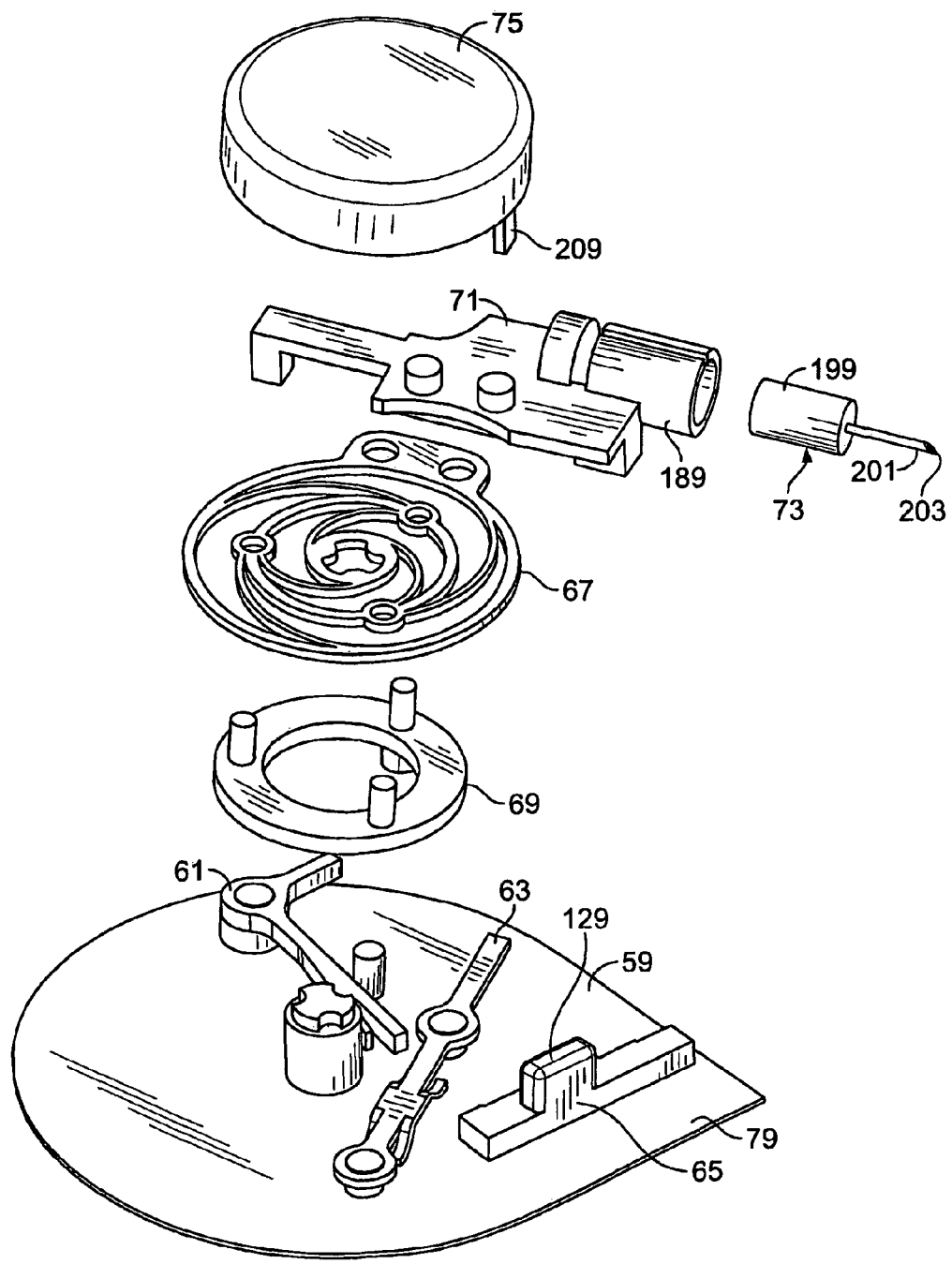
FIG. 4 is a left side, front, partially exploded perspective view of selected internal components disposed within the first compartment of the housing shown in FIG. 1.

Referring now to the drawings, there is shown in FIGS. 1 and 2, a first embodiment of a lancing device which is constructed according to the teachings of the present invention, the lancing device being identified generally by reference numeral 11. As will be described further below, selected components of lancing device 11 are used to fire a lancet into the skin of a patient to acquire a blood sample and selected components of lancing device are used to calculate and display the concentration of a particular analyte (e.g., glucose) in the acquired blood sample.

Lancing device 11 comprises a housing 13 constructed of a rigid and durable material, such as molded plastic. Housing 13 includes a base 15 and a cover 17 pivotally mounted to base 15 about a hinge 19. As such, cover 17 is capable of being pivoted between an open position, as shown in FIG. 1, and a closed position, as shown in FIG. 2. With cover 17 disposed in its closed position, as shown in FIG. 2, housing 13 has an overall length L of approximately 3.125 inches, an overall width W of approximately 1.875 inches and a overall thickness T of approximately 0.813 inches.

Base 15 includes a substantially flat front surface 21, a slightly rounded back surface 23, a top end 25, and a bottom end 27. Preferably, base 15 is hollowed out so as to define a substantially enclosed interior cavity 29 therewithin, interior cavity 29 being sized and shaped to receive the various internal components for lancing device 11. A lateral partition 31 is preferably integrally formed onto bottom surface 23 of base 15 within interior cavity 29 so as to divide interior cavity 29 into a first compartment 33 and a second compartment 35, first compartment 33 being sized and shaped to receive the various components which are used to fire a lancet to acquire a blood sample and second compartment 35 being sized and shaped to receive the various components which are used, in conjunction with a conventional test strip, to calculate and digitally display the concentration of a particular analyte (e.g., glucose) in said blood sample, as will be described further in detail below.

Front surface 21 of base 15 is shaped to include a door 37 which is adapted to pivot relative to the remainder of front surface 21 about an internal hinge (not shown). In this manner, door 37 is capable of being pivoted open so as to provide the user with access into first compartment 33 of interior cavity 29. In particular, door 37 enables the user, prior to lancing, to install a conventional disposable lancet into a complimentary lancet holder or, after lancing, to remove and discard a used disposable lancet from its complimentary lancet holder, as will be described further below.

A small opening 39 which is generally circular in lateral cross-section is formed into bottom end 27 of base 15 and extends into communication with first compartment 33. As will be described further in detail below, opening 39 is sized and shaped to enable the sharpened tip of a disposable lancet located within first compartment 33 to penetrate therethrough during the lancing process. Preferably, the portion of base immediately surrounding opening 39 is slightly recessed, or indented, in order to ergonomically receive the finger of a patient. In this capacity, with the finger of a patient ergonomically disposed against opening 39, a disposable lancet located within interior cavity 29 can be fired through opening 39 so as to puncture the skin of the patient.

A slot 41 is similarly formed into top end 25 of base 15 and extends into communication with second compartment 35. As will be described further below, slot 41 is sized and shaped to enable a conventional analyte test strip (e.g., an electrochemical blood glucose test strip) to be inserted therethrough and into electrical engagement with a data communication device (e.g., a conventional test port) which is disposed within second compartment 35 of interior cavity 29. In this manner, the electrical response which results from the application of a blood sample onto a test strip can be measured and analyzed by lancing device 11 in order to calculate the concentration of a particular analyte in said blood sample.

As noted above, cover 17 is pivotally mounted on base 15 about hinge 19. Although not shown herein, it is to be understood that cover 17 could be modified in shape so as to enclose opening 39 and slot 41 when cover 17 is disposed in its closed position. If cover 17 were modified to create a watertight seal over opening 39 and slot when cover 17 is disposed in its closed position, lancing device 11 would become a waterproof unit, which is highly desirable.

Cover 17, which is pivotally mounted on base 15 about hinge 19, comprises a rear, or inner, surface 43 and a front, or outer, surface 45. As seen most clearly in FIG. 1, cover 17 is generally U-shaped in lateral and longitudinal cross-section. As a result, inner surface 43 of cover 17 is shaped to define a partially enclosed cavity 45 therewithin.

A lancet holder 47 is integrally formed onto inner surface 43 of cover 17 and is sized and shaped to releasably retain a disposable lancet therewithin. In addition, a clip 49 is integrally formed onto inner surface 43 of cover 17 and is sized and shaped to releasably retain one or more conventional analyte test strips therewithin. In this manner, a user is able to store within partially enclosed cavity 45 all of the supplies which are required in order to draw and test a blood sample using lancing device 11, which is highly desirable.

Cover 17 is pivotally mounted onto base 15 about hinge 19. In the present embodiment, hinge 19 comprises a pair of spaced apart tabs 51 which are integrally formed onto the left side edge of base 15 and a single tab 53 which is formed onto the left side edge of cover 17, single tab 53 being sized and shaped to be fittingly received between spaced apart tabs 55. Each of tabs 53 and 55 is sized and shaped to include an elongated longitudinal bore 57 along its length which is generally circular in lateral cross-section. Tabs 51 and 53 are aligned in such a manner so that the bores 57 defined therein are co-linearly aligned. A cylindircal pin (not shown) is extended through bore 57 in each of tabs 51 and 53 so as to hingedly connect cover 17 to base 15.

It should be noted that alternative means for hingedly connecting cover 17 to base 15 could be used (e.g., a living hinge) without departing from the spirit of the present invention.

Referring now to FIGS. 3-8, lancing device 11 comprises various mechanical components which are disposed within first compartment 33 of base 15 and which can be used to lance the skin of a patient, as will be described further in detail below. Specifically, lancing device 11 comprises a support 59, a ratchet 61 pivotally mounted on support 59, a latch 63 slidably mounted on support 59, a depth adjuster 65 slidably mounted on support 59, a torsion spring 67 fixedly mounted on support 59, a spring support 69 fixedly coupled to spring 67, a lancet holder 71 fixedly coupled to torsion spring 67, a lancet 73 removably mounted within lancet holder 71, and a manually activated mechanism 75 coupled to torsion spring 67 through spring support 69.

Figure 9:
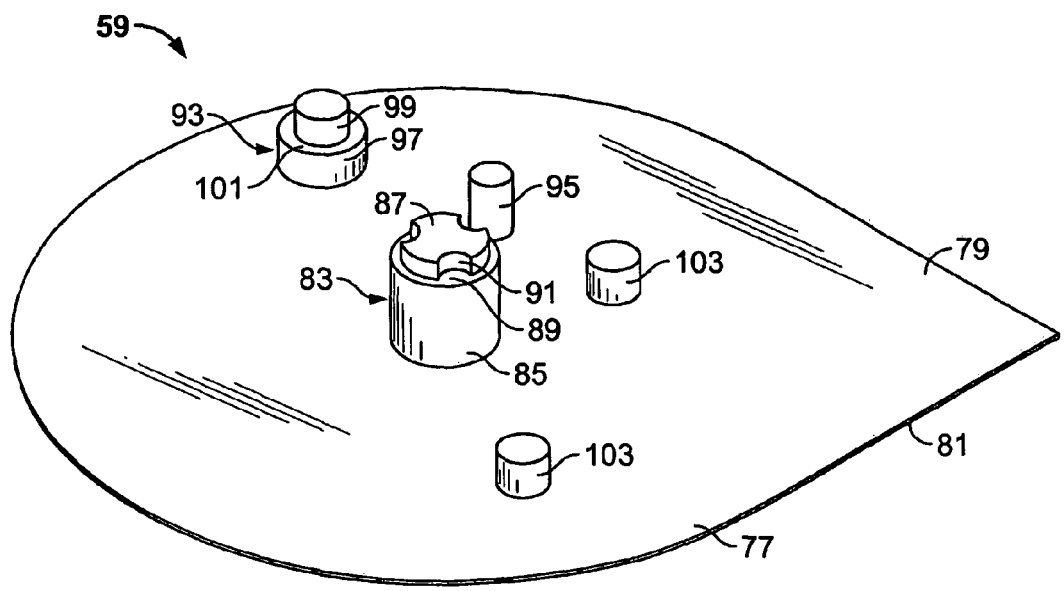
FIG. 9 is an enlarged, left side, front perspective view of the support shown in FIG. 3.

Support 59, which is shown separately in FIG. 9, serves as the foundation onto which most of the components located within first compartment 33 of base 15 are mounted, as will be described further in detail below. Preferably, support 59 is a unitary member which is constructed of plastic using conventional molding techniques, such as injection molding.

Support 59 is represented herein as being formed as a separate component which, in an additional manufacturing step, is affixed onto the inner surface of back surface 23 of base 15 within first compartment 33. However, it is to be understood that base 15 could alternatively be constructed with support 59 integrally formed onto the inner surface of back surface 23 within first compartment 33, such as through the process of injection molding, without departing from the spirit of the present invention.

Support 59 comprises a thin plate 77 comprising a substantially flat front surface 79 and a substantially flat back surface 81. Substantially flat back surface 81 is preferably permanently affixed onto inner surface of rounded back surface 23 of base 15 within first compartment 33. As noted above, rather than affix plate 77 onto base 15, support 59 and base 15 could, in the alternative, be molded as a single piece (e.g., using conventional injection molding techniques).

Figure 7:
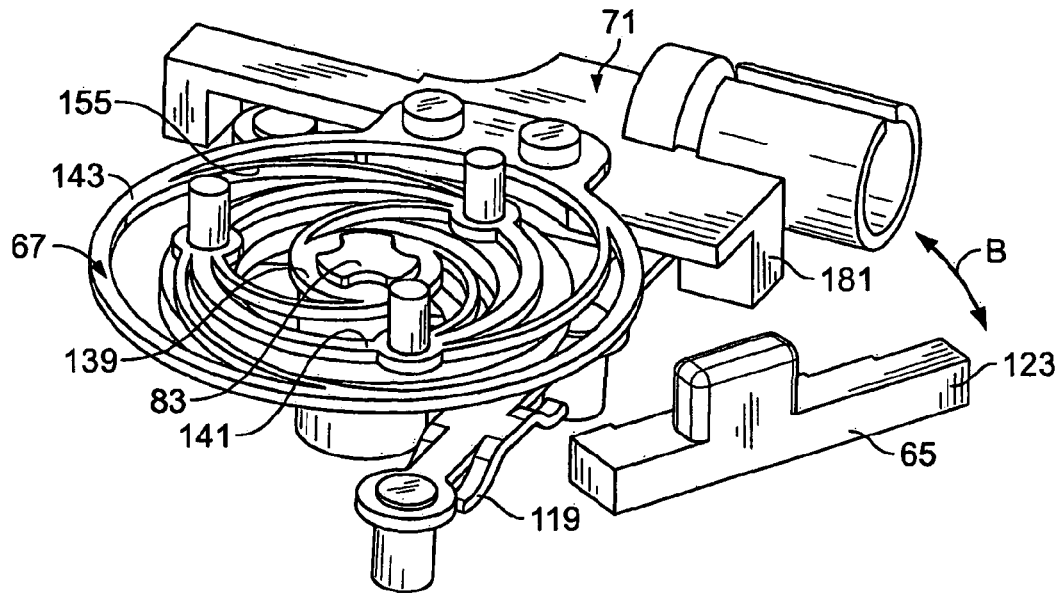
FIG. 7 is a left side, front perspective view of selected internal components disposed within the first compartment of the housing shown in FIG. 1.

A spring support post 83 is integrally formed onto front surface 79. Spring support post 83 is shaped to include a first portion 85 and a second portion 87. First portion 85 is generally cylindrical in shape and extends orthogonally out from front surface 79. Second portion 87 extends out from the free end of first portion 85 in co-axial alignment therewith. Second portion 87 has a width which is slightly less than the diameter of first portion 85. In this manner, a shelf 89 is created on the free end of first portion 85 around the periphery of second portion 87. As will be described further below, with lancet device 11 in its assembled form, torsion spring 67 is slidably mounted onto spring support 83 such that torsion spring 67 rests on shelf 89, as can be seen in FIG. 7.

It should be noted that second portion 87 is shaped to include a plurality of circular notches 91 which are equidistantly spaced along its outer periphery. As will be described further below, notches 91 serve to engage torsion spring 67 when mounted on spring support post 83 to preclude rotation of torsion spring 67 about spring support post 83.

A ratchet support post 93 and a ratchet stop 95 are also integrally formed onto front surface 79 of plate 77 in a spaced apart relationship. Ratchet support post 93 is shaped to include a first portion 97 and a second portion 99. First portion 97 is generally cylindrical in shape and extends orthogonally out from front surface 79. Second portion 99 is also cylindrical in shape and extends out from the free end of first portion 97 in co-axial alignment therewith. It should be noted that the diameter of second portion 99 is slightly less than the diameter of first portion 97. In this manner, an annular shelf 101 is created on the free end of first portion 97 around the periphery of second portion 99. As will be described further below, with lancet device 11 in its assembled form, ratchet 61 is pivotally mounted onto ratchet support post 93 such that ratchet 61 rests on shelf 101.

Ratchet stop 95 is generally cylindrical in shape. As will be described further below, with lancet device 11 in its assembled form, ratchet stop 95 is positioned to selectively limit the pivotal displacement of ratchet 61 about ratchet support post 93.

A pair of spaced apart latch support posts 103 are additionally integrally formed onto front surface 79 of plate 77 in a spaced apart relationship. Each of latch support posts 103 is generally cylindrical in shape and extends orthogonally out from front surface 79. As will be described further below, with lancet device 11 in its assembled form, latch 63 is slidably mounted on latch support posts 103.

Figure 10:
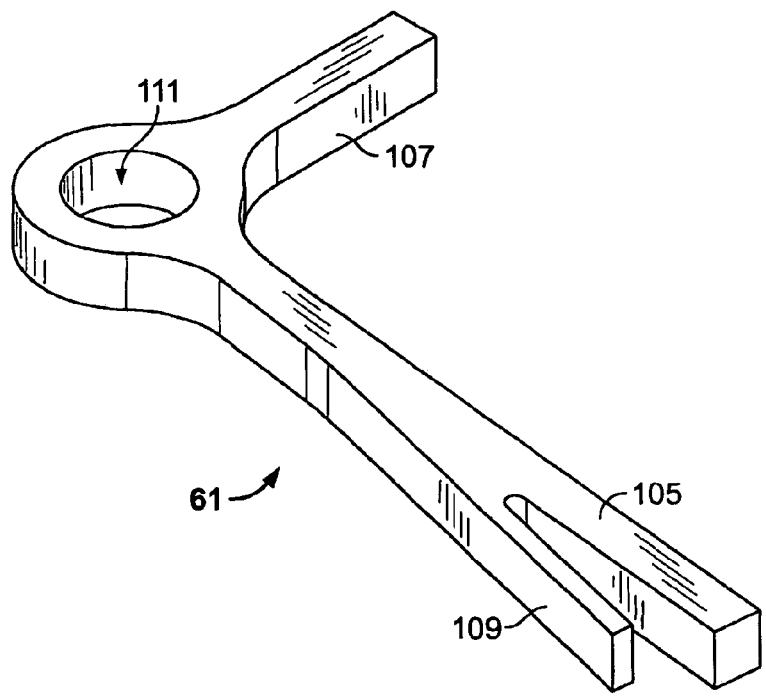
FIG. 10 is an enlarged, left side, front perspective view of the ratchet shown in FIG. 3.

Ratchet 61, which is shown separately in FIG. 10, is a unitary member which is manufactured preferably of plastic or spring steel. Ratchet 61 includes a first arm 105 and a second arm 107 which are orthogonally disposed in an L-shaped configuration.

A spring arm 109 is formed onto first arm 105, spring arm 109 extending out from first arm 105 at an acute angle. Spring arm 109 is constructed to have a limited cross sectional area. As a result, the free end of spring arm 109 is capable of being pivoted, or flexed, towards the free end of first arm 105 upon the application of a suitable inward force thereon. Upon termination of said inward force, spring arm 109 is designed to resiliently pivot back to its original position.

Ratchet 61 is shaped to define an opening 111 at the junction of first arm 105 and second arm 107. Opening 111 is generally circular in lateral cross-section and is sized and shaped to fittingly receive second portion 99 of ratchet support post 93. With lancing device 11 in its assembled form, ratchet 61 is slidably mounted onto ratchet support post 93 such that second portion 99 of ratchet support post 93 projects through opening 111. As such, ratchet 61 is seated in contact against shelf 101 and is capable of pivotal displacement. However, it is to be understood that ratchet stop 95 is positioned to selectively contact first arm 105 when ratchet 61 is rotated about second portion 99 of ratchet support post 93, thereby limiting the degree of rotation of ratchet 61.

Figure 11A:
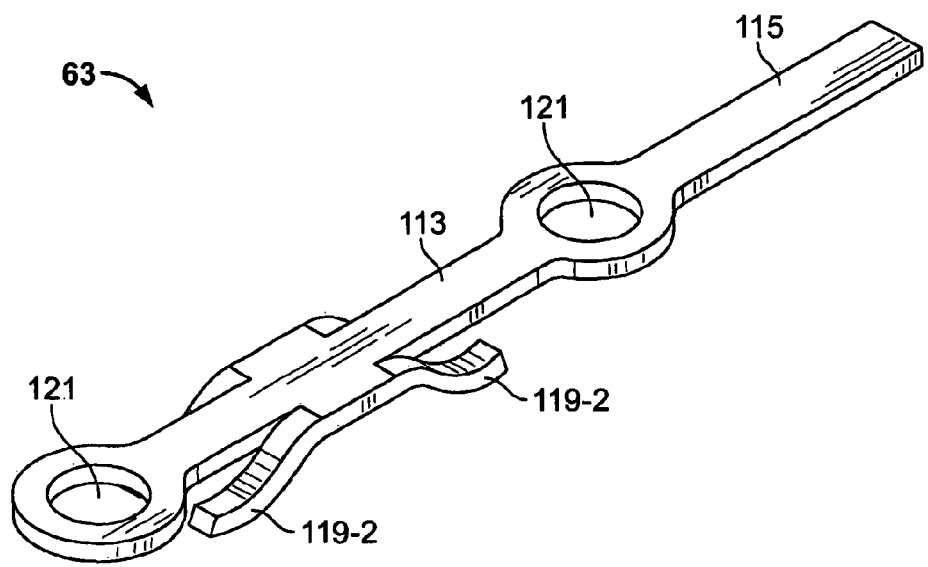
FIGS. 11(a) and (b) are enlarged front and back perspective views of the latch shown in FIG. 3.
Figure 11B:
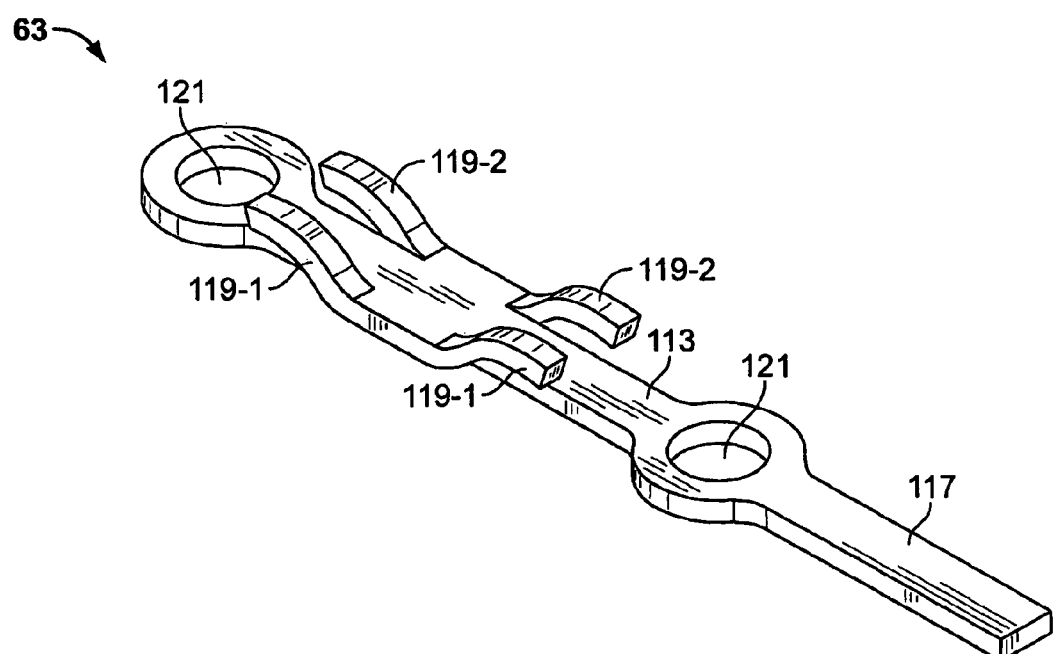

Latch 63, which is shown separately in FIGS. 11(a) and 11(b), is a unitary member which is manufactured preferably of plastic or spring steel. Latch 63 comprises an elongated arm 113 which includes a substantially flat front surface 115 and a substantially flat back surface 117.

First and second pairs of spring fingers 119-1 and 119-2, respectively, are formed onto opposite sides of arm 113, each pair of spring fingers 119 projecting down from arm 113 and away from each other. Each spring finger 119 is constructed to allow for its compression, or flattening, upon the application of a considerable downward force onto front surface 115 of arm 113. However, due to the resilient nature of each spring finger 119, upon removal of said downward force onto arm 113, each spring finger 119 returns back to its original configuration.

Arm 113 is shaped to define a pair of spaced apart openings 121. Each opening 121 is generally circular in lateral cross-section and is sized and shaped to fittingly receive an associated latch support post 103, as seen most clearly in FIG. 4. With lancing device 11 in its assembled form, latch 63 is slidably mounted onto support 59 such that latch support posts 103 project through openings 121, with spring fingers 119 drawn into contact against front surface 79 of plate 77. As can be appreciated, the application of a considerable downward force onto front surface 115 of arm 113 causes spring fingers 119 to flatten, or compress, which, in turn, causes arm 113 of latch 63 to be displaced axially along posts 103 in the direction towards front surface 79 of plate 77. Upon the removal of the application of said downward force, spring fingers 119 return to their original configuration which, in turn, causes arm 113 to be displaced axially along posts 103 in the direction away from front surface 79 of plate 77.

Figure 12:
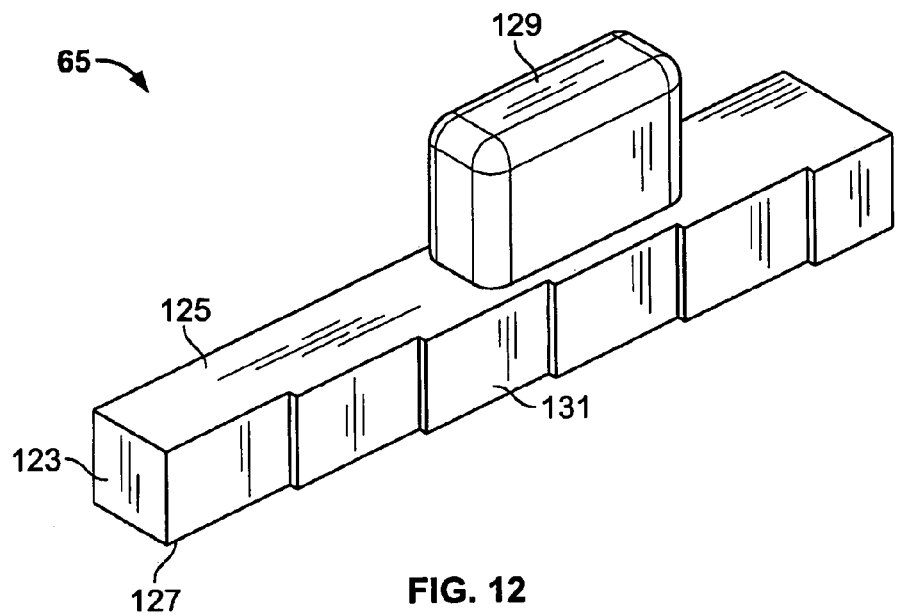
FIG. 12 is an enlarged top, front perspective view of the depth adjuster shown in FIG. 3.

Depth adjuster 65, which is shown separately in FIG. 12, is a unitary member which is manufactured preferably of plastic. Depth adjuster 65 comprises a solid block 123 which includes a front surface 125 and a back surface 127. A finger actuation tab 129 is formed onto and extends orthogonally out from front surface 125 of block 123 and serves to allow the user linearly slide depth adjuster 65 within first compartment 33 of interior cavity 29 of base 15. As will be described further below, depth adjuster 65 can be linearly displaced to regulate the depth of the penetration of lancet 73 into the finger of the patient during firing.

Block 123 includes a multi-stepped surface 131 which provides block 123 with a varying width along its length. It should be noted that the various faces of multi-stepped surface 131 are disposed in parallel planes with one another. As will be described further in detail below, during the firing stroke for lancet device 11, a portion of lancet holder 71 is positioned so as to abut against one face of multi-stepped surface 131, thereby limiting further displacement of lancet holder 71 and, in turn, lancet 73.

With lancet device 11 in its assembled form, back surface 127 of block 123 is disposed in direct contact against front surface 79 of plate 77. It should be noted that tab 129 is sized and shaped to fittingly protrude through an elongated rectangular slot 133 which is formed in flat front surface 21 of base 15. Slot 133 is sized and shaped to allow depth adjuster 65 to be slid upon top surface 79 of plate 77 along a linear path, as represented by arrow A in FIG. 1. The linear displacement of depth adjuster 65 determines which face of multi-stepped surface 131 is aligned to contact lancet holder 71 during the firing stroke of lancet device 11. As can be appreciated, the particular face against which lancet holder 71 abuts during the firing stroke, in turn, determines the relative depth which lancet 73 penetrates into the skin of the patient.

Figure 13A:
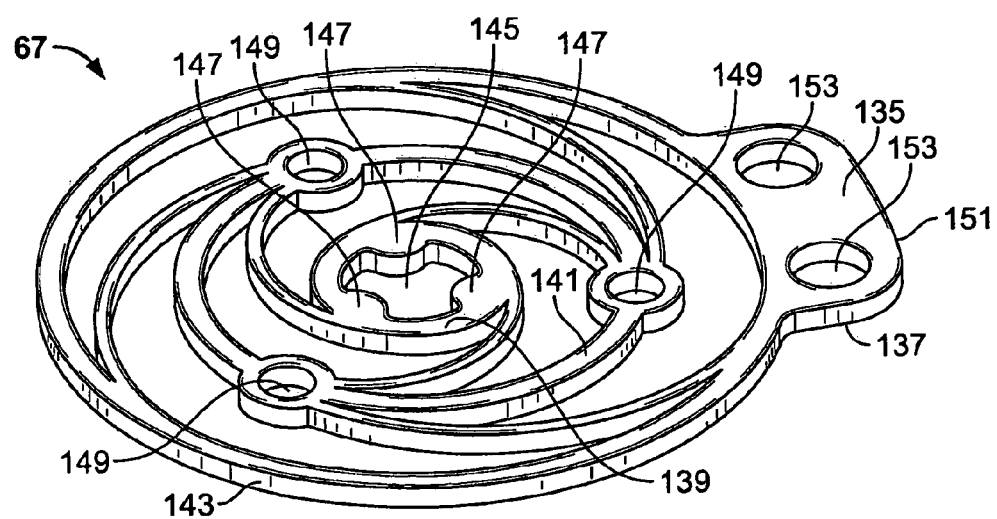
FIG. 13(a) is an enlarged, bottom, front perspective view of the torsion spring shown in FIG. 3.
Figure 13B:
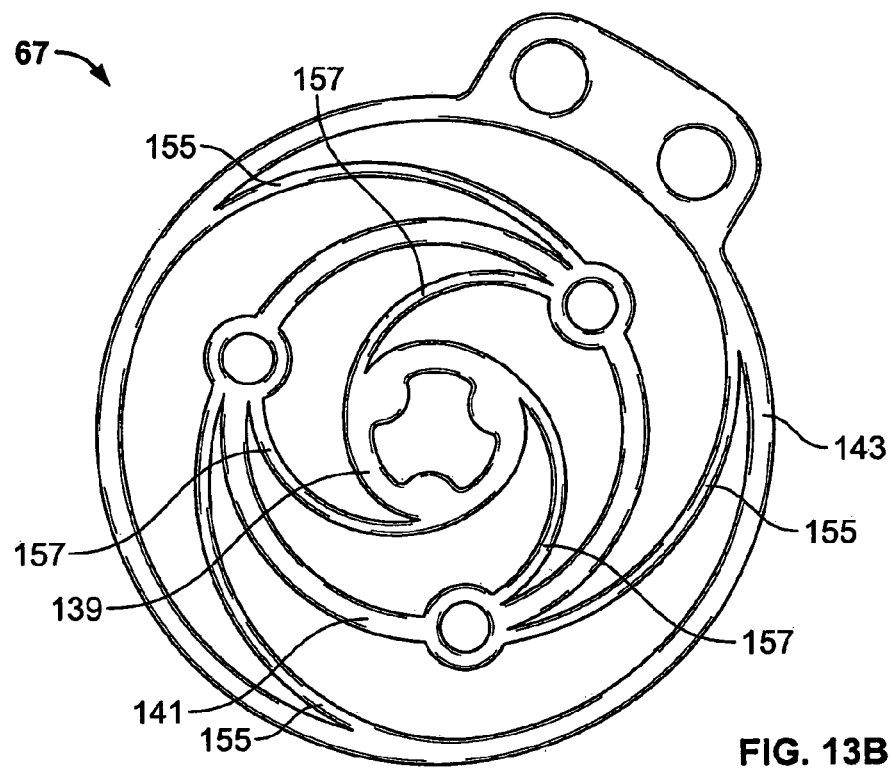
FIG. 13(b) is a front plan view of the torsion spring shown in FIG. 13(a), said torsion spring being shown with each activation arm configured in its de-energized state.
Figure 13C:
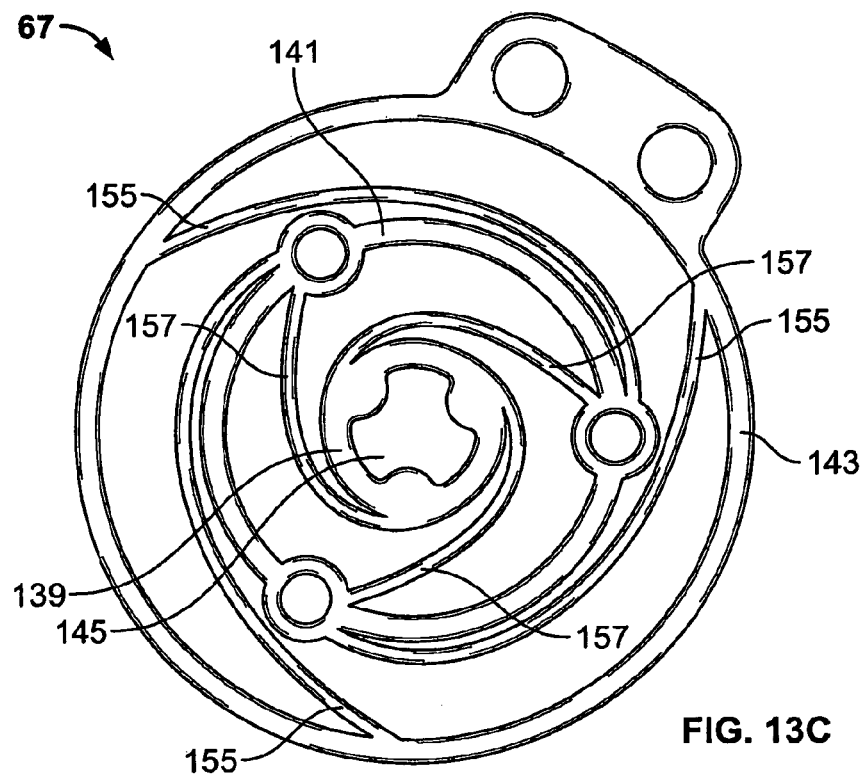
FIG. 13 (c) is a front plan view of the torsion spring shown in FIG. 13(b), said torsion spring being shown with each activation arm configured in its energized state.

Torsion spring 67, which is shown separately in FIGS. 13(a)-(c), is a unitary member which is preferably constructed of plastic or spring steel. Torsion spring 67 is generally planar and includes a substantially flat front surface 135 and a substantially flat back surface 137. Torsion spring 67 additionally includes an inner ring 139, a middle ring 141, and an outer ring 143 which are all concentrically configured.

Inner ring 139 is generally annular and is shaped to define a central opening 145. Inner ring 139 includes a plurality of inwardly protruding ribs 147 which are spaced equidistantly apart from one another. Inner ring 139 is sized and shaped to be slidably and fittingly mounted onto second portion 87 of spring support post 83 with back surface 137 of inner ring 139 disposed in contact against shelf 89 of spring post 83. With lancet device 11 in its assembled form, inner ring 139 is mounted on spring support post 83 such that each rib 147 fittingly protrudes into a corresponding notch 91 to preclude the rotation of inner ring 139 relative to spring support post 83.

Middle ring 141 is generally annular and is shaped to define a plurality of openings 149 which are spaced equidistantly apart from one another. Each opening 149 is generally circular in lateral cross-section and is sized and shaped to fittingly receive a corresponding post formed on spring support 69, as will be described further in detail below.

Outer ring 143 is generally annular and is shaped to include an outwardly protruding tab 151. Tab 151 is shaped to define a pair of spaced apart holes 153. Each hole 153 is generally circular in lateral cross-section and is sized and shaped to fittingly receive a corresponding post formed on lancet holder 71, as will be described further below.

Outer ring 143 is connected to middle ring 141 through a plurality of activation spring arms 155. Activation spring arms 155 are integrally formed along the inner periphery of outer ring 143 and extend in an arcuate path towards middle ring 141. As seen most clearly in FIG. 13(b), activation spring arms 155 are spaced equidistantly apart from one another and extend in an arcuate, generally clockwise path from outer ring 143 to middle ring 141.

It should be noted that, with outer ring 143 held fixed in place, the application of a rotational force on middle ring 141 in the clockwise direction approximately 30 degrees relative to outer ring 143 causes each activation spring arm 155 to transform from its original, de-energized state, as shown in FIG. 13(b), to an energized state, as shown in FIG. 13(c). As can be seen in FIGS. 13(b) and (c), the transformation of activation spring arms 155 from their de-energized state to their energized state causes each activation spring arm 155 to be drawn inward towards middle ring 141. Due its resilient construction, each activation spring arm 155 is naturally biased to return to its original configuration (i.e., its de-energized state). In this manner, energy can be stored into activation spring arms 155 through the application of a rotation force on middle ring 141 relative to outer ring 143. As will be described further below, the release of energy stored in activation spring arms 155 can be used to rotatably fire outer ring 143 in the clockwise direction which, in turn, can be used to advance lancet 73 out through opening 39 in base 15.

Middle ring 141 is connected to inner ring 139 through a plurality of return spring arms 157. Return spring arms 157 are integrally formed along the inner periphery of middle ring 141 and extend in an arcuate path towards inner ring 139. As seen most clearly in FIG. 13(b), return spring arms 157 are spaced equidistantly apart from one another and extend in an arcuate, generally counterclockwise path from middle ring 141 to inner ring 139.

It should be noted that, with inner ring 139 held fixed in place, the application of a rotational force on middle ring 141 in the clockwise direction approximately 30 degrees relative to inner ring 139 causes each return spring arm 157 to transform from its original, de-energized state, as shown in FIG. 13(b) to an energized state, as shown in FIG. 13(c). As can be seen in FIGS. 13(b) and (c), the transformation of return spring arms 157 from their de-energized state to their energized state causes each return spring arm 157 to significantly flatten. Due to its resilient construction, each return spring arm 157 is naturally biased to return to its original configuration (i.e., its de-energized state). In this manner, energy can be stored into return spring arms 157 through the application of a rotation force on middle ring 141 relative to inner ring 139. As will be described further below, the release of energy stored in return spring arms 157 can be used to rotatably fire middle ring 141 in the counterclockwise direction which, in turn, can be used to retract lancet 73 after the forward firing stroke.

It should be noted that torsion spring 67 is constructed in such a manner so that activation spring arms 155 and return spring arms 157 can be independently energized and de-energized. In other words, activation spring arms 155 can be transformed between its energized and de-energized states independent of the state of return spring arms 157 and similarly, return spring arms 157 can be transformed between its energized and de-energized states independent of the state of activation spring arms 155.

It should also be noted that activation spring arms 155 and return spring arms 157 extend arcuately inward in opposite directions. As a result, the release of energy stored in one set of spring arms (e.g., activation spring arms 155) can be used to fire lancet 73 forward from a retracted position to an extended position and the release of energy stored in the other set of spring arms (e.g., return spring arms 157) can be used to pull lancet 73 backward from an extended position back to a retracted position, as will be described further below.

Figure 14A:
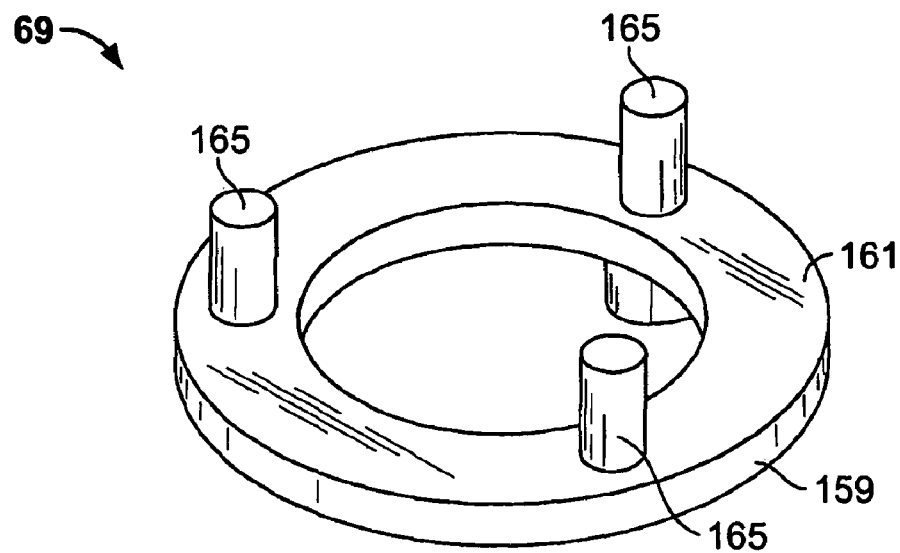
FIGS. 14(a) and (b) are enlarged front and rear perspective views, respectively, of the spring support shown in FIG. 3.

Spring support 69, which is shown separately in FIGS. 14(a) and (b), is a unitary member which is preferably constructed of plastic. It should be noted that spring support 69 and torsion spring 67 could be molded together as a single piece without departing from the spirit of the present invention.

Spring support 69 comprises an annular disk 159 which is shaped to include a substantially flat front surface 161 and a substantially flat back surface 163. A plurality of posts 165 are integrally formed onto and extend orthogonally away from front surface 161 of disk 159, posts 165 being spaced equidistantly apart from one another. Each post 165 is generally circular in lateral cross-section and is sized and shaped to fittingly protrude through an associated opening 149 in middle ring 141 of torsion spring 67. In this manner, with lancet device 11 in its assembled form, torsion spring 67 is mounted on spring support 69 by disposing back surface 137 of middle ring 141 of torsion spring 67 in direct contact against front surface 161 of disk 159 of spring support 69, torsion spring 67 being aligned such that posts 165 on spring support fittingly project through corresponding openings 149 in torsion spring 67, thereby fixedly coupling middle ring 141 of torsion spring 67 and spring support 69 together (as seen most clearly in FIG. 7).

Figure 14B:
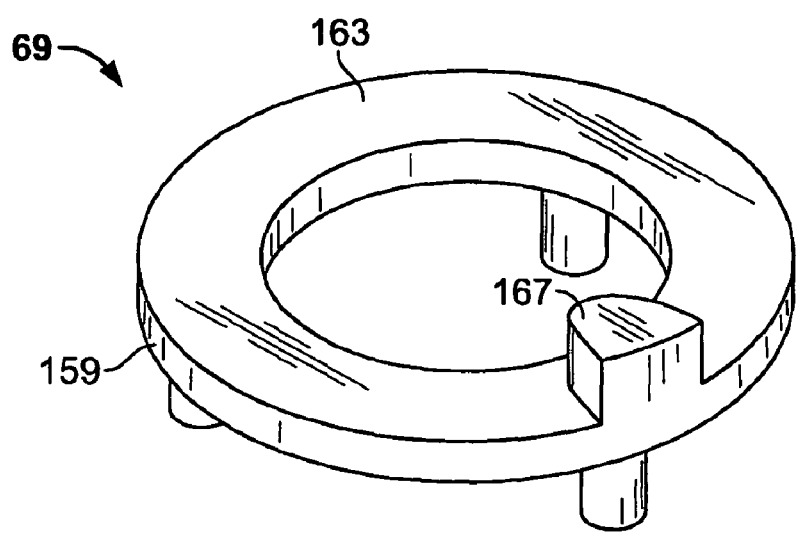

A ratchet lock 167 is integrally formed onto and extends orthogonally away from back surface 163 of annular disk 159, as seen most clearly in FIG. 14(b). As will be described, further in detail below, ratchet lock 167 is sized and shaped to be selectively engaged by first arm 105 of ratchet 61 to retain, or lock, middle ring 141 in its cocked position (i.e., with both activation spring arms 155 and return spring arms 157 in their energized states).

Lancet holder 71, which is shown separately in FIGS. 15(a) and (b), is a unitary member which is preferably constructed of a durable molded plastic or another similarly suitable material. It should be noted that lancet holder 71 and torsion spring 67 (as well as spring support 69) could be molded together as a single piece without departing from the spirit of the present invention.

Lancet holder 71 comprises a base 169 which includes a substantially flat front surface 171 and a substantially flat back surface 173.

A pair of spaced apart posts 175 are integrally formed onto and extend orthogonally away from front surface 171 of base 169. Each, post 175 is generally circular in lateral cross-section and is sized and shaped to fittingly protrude through an associated hole 153 in tab 151 of torsion spring 67. Accordingly, with lancet device 11 in its assembled form, torsion spring 67 is mounted on lancet holder 71 by disposing back surface 137 of tab 151 in direct contact against front surface 171 of base 169 of lancet holder 71, torsion spring 67 being aligned such that posts 175 on lancet holder 71 fittingly project through corresponding holes 153 in torsion spring 67, thereby coupling outer ring 143 of torsion spring 67 with lancet holder 71 (as seen most clearly in FIG. 5).

A projection 177 which is generally rectangular in lateral cross-section protrudes orthogonally out from back surface 173 of base 169, as seen most clearly in FIG. 15(b). Projection 177 is shaped to include a flat contact surface 179 which is adapted to slide on top of front surface 79 of plate 77, thereby enabling lancet holder 71 to slidably travel along an arcuate path within base 15, as will be discussed further below. Projection 177 is also shaped to include a flat abutment surface 181 at its leading end, surface 181 being sized and shaped to selectively contact one face of the multi-stepped surface 131 of depth adjuster 65 so as to limit the penetration of lancet 73 out through opening 39 in base 15.

A notch 183 is formed into contact surface 179 of projection 177 proximate abutment surface 181. Notch 183 is generally rectangular in lateral cross-section and is sized and shaped to receive the free end of arm 113 of latch 63, as seen most clearly in FIG. 8. In this manner, latch 63 can be used to selectively retain, or lock in place, the position of lancet holder 71 within base 15, as will be described further in detail below.

In addition, a recess 185 is similarly formed into contact surface 179 of projection. 177 in a spaced apart relationship from notch 183, recess 185 serving to define a tail 187 at the trailing end of projection 179. Recess 185 is generally rectangular in lateral cross-section and is sized and shaped to receive second arm 107 of ratchet 61 when lancet device 11 is in its assembled form. In this manner, the displacement of lancet holder 71 eventually causes lancet holder 71 to contact second arm 107 and, in turn, pivot ratchet 61 about ratchet support post 93, as will be described further in detail below.

A generally tubular structure 189 is integrally formed onto base 169 along its leading end. Tubular structure 189 is in the form of a cylinder which includes an open leading end 191 and a closed trailing end 193. Tubular structure 189 is hollowed so as to define a longitudinal bore 195 along its length. As can be appreciated, tubular structure 189 is sized and shaped such that lancet 73 can be fittingly disposed within bore 195. Preferably, tubular structure 189 is provided with a narrow slot 197 along its length to enable structure 189 to flex slightly when receiving lancet 73.

Lancet 73 is preferably of the conventional, disposable variety. Specifically, lancet 73 comprises a cylindrical base 199 and a stem 201. Base 199 is removably received within bore 195 of lancet holder 71. Stem 201 of lancet 73 extends outwardly from base 199 and is sized and shaped to fittingly penetrate through opening 39 formed in bottom 27 of base 15. Stem 201 terminates in a sharp tip 203 which is adapted to pierce the skin of a patient.

Figure 6:
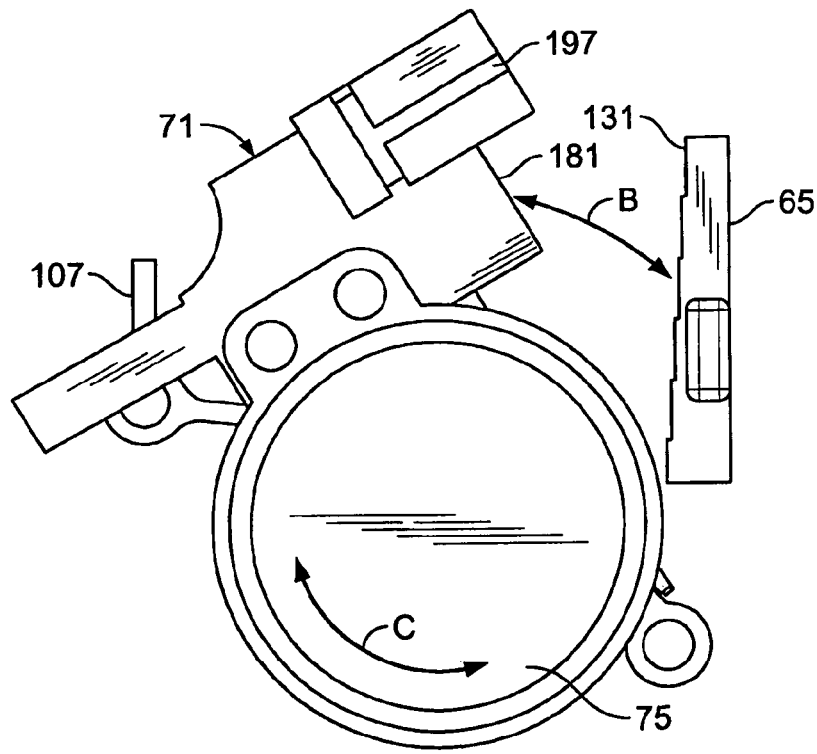
FIG. 6 is a front plan view of the selected internal components shown in FIG. 5.

It should be noted that lancet holder 71 is capable of being slidably displaced within interior cavity 29 of base along an arcuate path which is represented by arrow B in FIGS. 6 and 7. Specifically, lancet holder 71 is capable of displacement such that lancet 73, in turn, travels between a retracted position in which sharp tip 203 of lancet 73 is positioned entirely within base 15 and an extended position in which sharp tip 203 of lancet 73 protrudes out from base 15. As will be described further below, the release of energy stored in activation spring arms 155 serves to fire lancet 73 from its retracted position to its extended position. Further, the release of energy stored in return spring arms 157 serves to pull lancet from its extended position back to its retracted position.

Figure 16A:
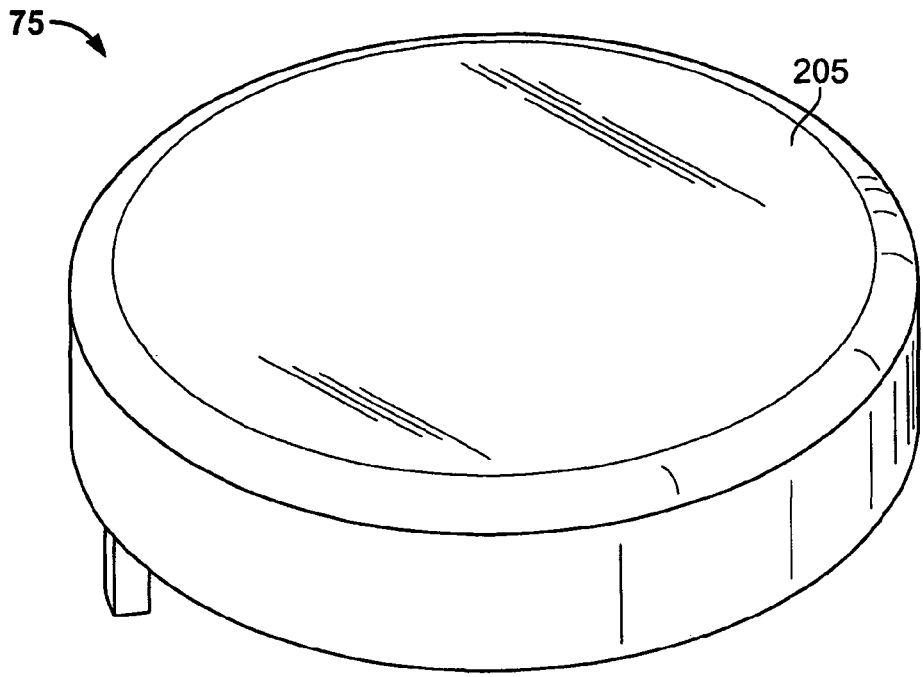
FIGS. 16(a) and (b) are enlarged front and rear perspective views, respectively, of the manually activated mechanism shown in FIG. 3.
Figure 16B:
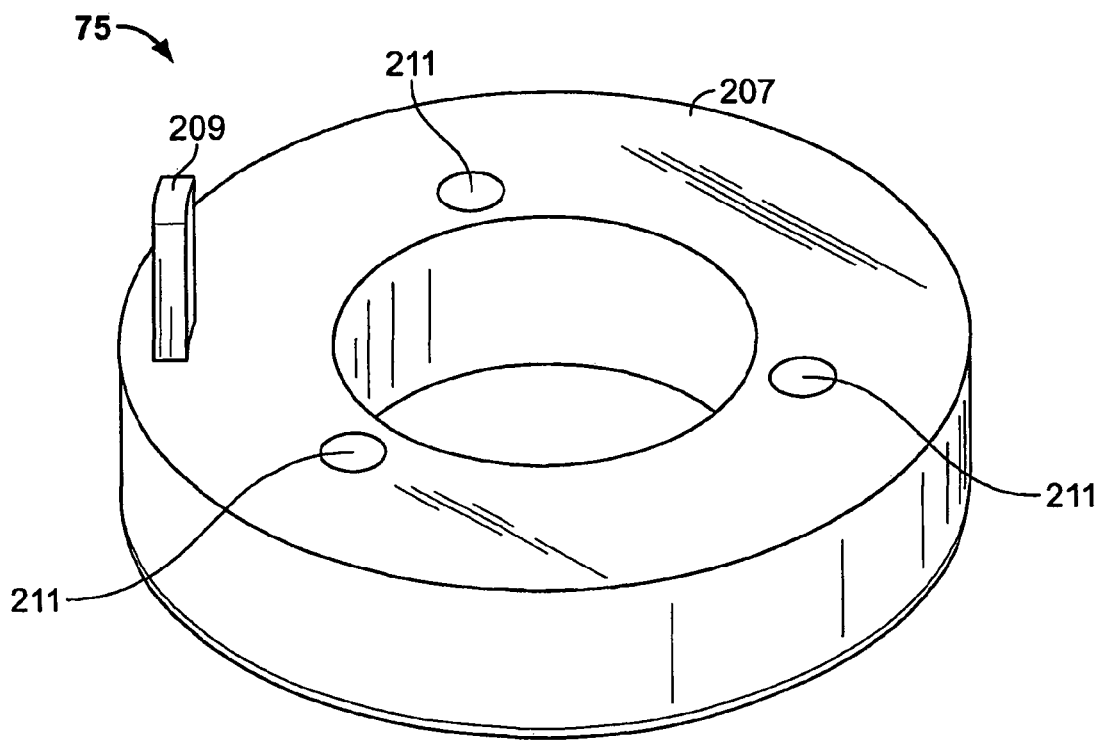

A single manually activated mechanism 75, which is shown separately in FIGS. 16(a) and (b), is provided to enable the user to both energize torsion spring 67 and fire lancet 73 out from base 15. Manually activated mechanism 75 is represented herein as being in the form of a one-piece button which is preferably constructed of a durable molded plastic or other suitable material. However, it is to be understood that mechanism 75 is not limited to being in the form of a button. Rather, mechanism 75 could alternatively be in the form of any similar manually activated device, such as a knob or trigger, without departing from the spirit of the present invention.

Figure 5:
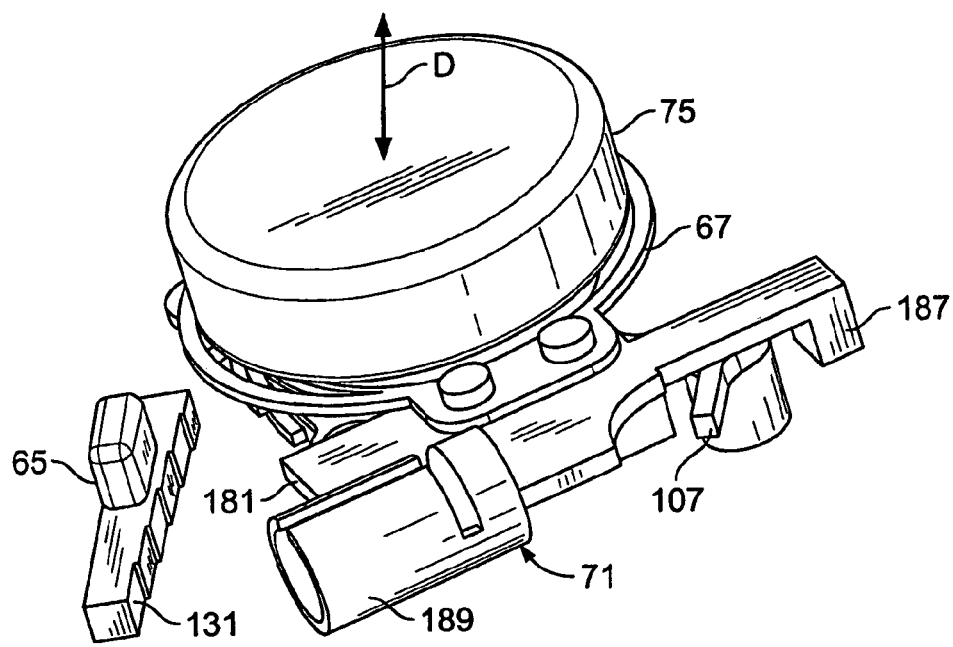
FIG. 5 is a right side, front perspective view of selected internal components disposed within the first compartment of the housing shown in FIG. 1.

Mechanism 75 includes a substantially flat front surface 205 and a substantially flat rear surface 207. A post 209 is integrally formed onto and extends orthogonally out from rear surface 207. In addition, a plurality of holes 211 are formed into rear surface 207 of button 75, holes 211 being spaced equidistantly apart from one another. Each hole 211 is generally circular in lateral cross-section and is sized and shaped to receive an associated post 165 of spring support 69, as shown in FIG. 5. Accordingly, with lancet device 11 in its assembled form, posts 165 on spring support 69 penetrate through openings 149 in torsion spring 67 and, in turn, project into holes 211 in mechanism 75.

Front surface 205 of mechanism 75 is sized and shaped to fittingly penetrate through a corresponding circular opening 213 which is formed in front surface 21 of base 15. In this manner, front surface 205 of mechanism 75 is accessible by the user to energize torsion spring 67 and fire lancet 73 out from base 15. It should be noted that a plurality of notches (not shown) may be formed into front surface 205 of mechanism 75 along its outer periphery to facilitate its handling without departing from the spirit of the present invention.

It should noted that, with lancing device 11 configured in its assembled form, mechanism 75 is capable of being both: (1) rotated in the clockwise direction about spring support post 83, as represented by arrow C in FIGS. 1 and 6, and (2) displaced axially along spring support post 83, as represented by arrow D in FIG. 5. As will be described further below, rotation of mechanism 75 in the clockwise direction approximately 30 degrees serves to energize torsion spring 67. Further, depression of mechanism 75 along the longitudinal axis of spring support post 83 serves to fire lancet 73 out from base 15.

Configured into its fully assembled form, lancing device 11 may be used in the following manner to acquire a blood sample. Specifically, cover 17 is first pivoted open so as to enable the user to effectively utilize lancet device 11. With cover 17 open, door 37 in front panel 21 of base 15 is pivoted open, thereby providing the user with access into first compartment 33 of interior cavity 29. Lancet 73, which is preferably stored within lancet holder 47 of cover 17, is removed therefrom and is mounted in bore 195 of lancet holder 71. With lancet 73 properly installed, door 37 is pivoted closed. Configured as such, lancet 73 is originally disposed in its retracted position (i.e., with sharp tip 203 contained entirely within base 15).

In order to energize lancet device 11 for subsequent lancing, the user is required to rotate mechanism 75 in the clockwise direction approximately 30 degrees (i.e., in the direction represented by arrow C). It should be noted that, during the process of rotating mechanism 75, inner ring 139 of torsion spring 67 is held fixed in place by spring support post 83, as seen most clearly in FIG. 7, and outer ring 143 of torsion spring 67 is held fixed in place by lancet holder 71 which, in turn, is held fixed in place by arm 113 of latch 67, as seen most clearly in FIG. 8. Accordingly, the rotation of mechanism 75 serves only to rotate spring support 69 which, in turn, serves to only similarly rotate middle ring 141 of torsion spring 67. As can be appreciated, the rotation of middle ring 141 of torsion spring 67 in the clockwise direction approximately 30 degrees, with inner ring 139 and outer ring 143 held fixed in place, serves to transform activation spring arms 155 and return spring arms 157 from their original de-energized states, as shown in FIG. 13(*b*), to their energized states, as shown in FIG. 13(*c*).

Figure 8:
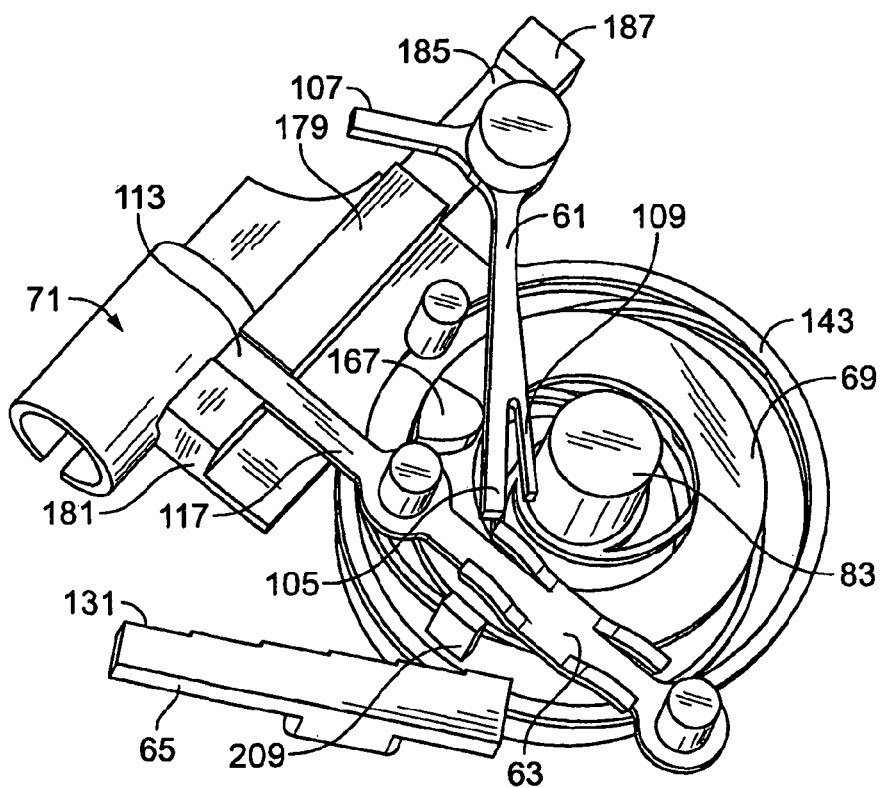
FIG. 8 is a back perspective view of selected internal components disposed within the first compartment of the housing shown in FIG. 1.

As seen most clearly in FIG. 8, during the rotation of spring support 69, ratchet lock 167 on spring support 69 is drawn into contact against the outer surface of first arm 105, with spring arm 109 of ratchet 61 disposed in contact against spring support post 83. The contact between ratchet lock 167 and first arm 105 as well as the contact between spring arm 109 and spring support post 83 causes first arm 105 and spring arm 109 of ratchet 61 to pivot towards one another. Continued rotation of spring support 69 in the clockwise direction (which is the counterclockwise direction when viewed from underneath in FIG. 8) causes ratchet lock 167 to travel along the length of first arm 105 of ratchet 61. When spring support 69 rotates approximately 30 degrees, ratchet lock 167 extends past the free end of first arm 105 of ratchet 61. As a result, the compressive energy stored between first arm 105 and spring arm 109 of ratchet 61 causes first arm 105 to resiliently pivot outward. Accordingly, once the user stops rotating mechanism 75, activation spring arms 155 and return spring arms 157 of torsion spring 67 are biased to resiliently return to their original, de-energized state which, in turn, drives middle ring 141 in the counterclockwise direction. However, as middle ring 141 is driven back in the counterclockwise direction (which is the clockwise direction when viewed from underneath in FIG. 8), ratchet lock 167 on spring support 69 abuts against the free end of first arm 105 of ratchet 61. As a result, spring support 69 and, in turn, middle ring 141 of torsion spring 67 are locked in place, thereby storing the energy contained within activation spring arms 155 and return spring arms 157.

With inner ring 139, middle ring 141, and outer ring 143 of torsion spring 67 fixedly locked in place while activation spring arms 155 and return spring arms 157 are configured in their energized state, as shown in FIG. 13(*c*), lancet device 11 is properly loaded for lancing. The user is then required to position his/her finger against bottom end 27 of base 15 so as to cover opening 39.

In order to fire lancet 73 through opening 39, the user is required to depress mechanism 75 axially towards back surface 23 of base 15. The depression of mechanism 75 draws post 209 into contact against front surface 115 of latch 63. As mechanism 75 is urged further downward, post 209 applies a downward force onto front surface 115 of latch 63 which, in turn, causes first and second spring fingers 119 to flatten, thereby drawing elongated arm 113 downward towards back surface 23 of base 15. As seen most clearly in FIG. 8, the displacement of elongated arm 113 towards back surface 23 of base 15 causes the free end of arm 113 to disengage from within notch 183 of lancet holder 71. As a result, latch 63 no longer retains lancet holder 71 fixed in place. With lancet holder 71 disengaged from latch 63, outer ring 143 of torsion spring 67 is similarly no longer held locked in place.

With outer ring 143 of torsion spring 67 now free to rotate, the energy stored within activation spring arms 155 is able to be released independently of return spring arms 157. As noted above, activation spring arms 155 are naturally biased to return to their de-energized state. Accordingly, as activation spring arms 155 return to their de-energized state, activation spring arms 155 drive outer ring 143 in the clockwise direction. The rotation of outer ring 143 similarly drives lancet holder 71 which, in turn, fires lancet 73 in an arcuate path (represented by arrow B in FIGS. 6 and 7) from its retracted position to its extended position. Specifically, lancet 73 travels until sharp tip 203 protrudes through opening 39 in bottom end 27 of base 15 and into the finger of the patient.

It should be noted that as lancet 73 is fired from its retracted position to its extracted position, abutment surface 181 of lancet holder 71 eventually contacts a corresponding face on multi-stepped surface 131 of depth adjuster 65, with lancet 73 traveling above block 123. The particular face on depth adjuster 65 which lancet holder 71 contacts (and accordingly the degree of motion of lancet 73) is dependent upon the linear position of depth adjuster 65.

As noted above, the release of energy stored in activation spring arms 155 serves to fire lancet 73 from its retracted position to its extended position. As seen most clearly in FIG. 8, as lancet 73 approaches its extended position, tail 187 on lancet holder 71 is drawn into contact against second arm 107 of ratchet 61 and, in turn, pivots second arm 107 of ratchet 61 inward towards spring support post 83. The rotation of ratchet 61 causes first arm 105 to similarly inward towards spring support post 83 which, in turn, disengages first arm 105 of ratchet 61 from ratchet lock 167. With ratchet 61 now disengaged from ratchet lock 167, middle ring 141 of torsion spring 67 is no longer held fixed in place.

With middle ring 141 of torsion spring 67 free to rotate, the energy stored within return spring arms 157 is able to be released independent of activation spring arms 155. As noted above, return spring arms 157 are naturally biased to return to their de-energized state. Accordingly, as return spring arms 157 return to their de-energized state, return spring arms 157 drive middle ring 141 and, in turn, outer ring 143, in the counterclockwise direction. The rotation of outer ring 143 in the counterclockwise direction similarly drives lancet holder 71 in the clockwise direction which, in turn, pulls lancet 73 in an arcuate path from its extended position back to its original retracted position. In this manner, sharp tip 203 of lancet 73 is positioned back within base 15 so as to prevent inadvertent subsequent contact, which is highly desirable.

Upon completion of the release of energy stored within return spring arms 157, lancet device 11 returns to its original configuration, thereby allowing for future use, which is highly desirable. As noted above, lancet 73 is capable of being removed from lancet holder 71, discarded and replaced with an unused lancet, as deemed necessary.

Having used lancet device 11 in the manner above to acquire a blood sample, it is to be understood that lancet device 11 is additionally designed to calculate and display the concentration of a particular analyte in the acquired blood sample, as will be described further below.

Specifically, due to the considerable compactness of the components used to lance the finger of a patient to acquire a blood sample, lancing device 11 is additionally capable of supporting electronic components for use in measuring the concentration of glucose in the blood sample without significantly increasing the overall size of lancing device 11. The majority of the various electronic components are preferably disposed within second compartment 35 of base 15.

Preferably, the various components which are typically found in a conventional analyte test instrument (ATI) used to measure the concentration of an analyte in a test sample are disposed within second compartment 29. For example, the various components which constitute a blood glucose monitor (e.g., an electrochemical or photometric blood glucose monitor) may be disposed within second compartment. As such, lancet device is provided with the capability of measuring glucose concentrations of a blood sample and, in turn, storing the results of each blood glucose measurement as data in memory.

Figure 17:
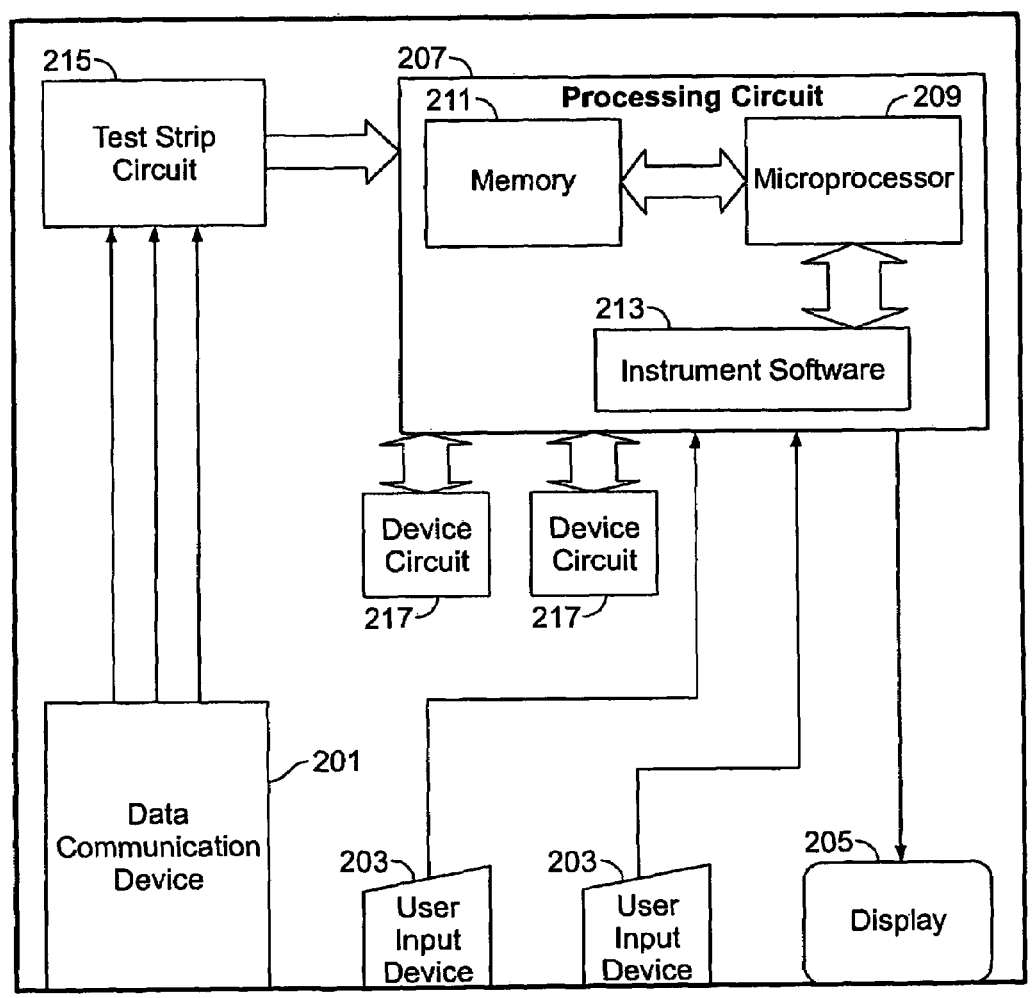
FIG. 17 is a schematic representation of selected internal components disposed within the second compartment of the housing shown in FIG. 1.

Referring now to FIG. 17, lancet device 11 preferably comprises a data communication device 201 which is disposed within second compartment 35 of interior cavity 29 of housing 13 and which is accessible through slot 41 in base 15. Data communication device 201 is capable of transmitting and receiving serial data. In the present embodiment, data communication device 201 is in the form of a conventional multi-purpose test port which includes a slot shaped to matingly receive and electrically connect with, inter alia, a test strip, a calibration strip, or the interface connector of a hardwire communication link.

Lancet device 11 also comprises a pair of user input devices 203 which are disposed within second compartment 35 and which at least partially: project through associated openings formed in front surface 21 of base 15. Each user input device 203 is represented herein as being in the form of a button capable of being manually depressed. In use, input devices 203 can be used to perform selected operative functions for lancet device 11 (e.g., regulating the power state of lancet device 11, recalling information stored in memory, responding to messages provided in the display, providing access to menus generated by software contained therewithin, and setting some of the configuration control. parameters).

Lancet device 11 further comprises a display 205 which is disposed within second compartment 35 and which at least partially projects through an associated opening formed in front surface 21 of base 15. Display 205 is shown herein as being in the form of a screen designed to provide the user with information in a visual form. Preferably, display 205 is in the form of a liquid crystal display (LCD) which is used to display, inter alia, test results, user messages, and recalled information which is stored in the memory of lancing device 11. It should be noted that display 205 is preferably designed to include a numerical display which is capable of generating three, seven-segment digital numbers, the numerical display providing the user with a means for visually indicating the numerical value associated with a particular test result. Display 205 is also preferably designed to include a plurality of icons which indicate the units of measurement of a particular test result (e.g., mg/dL or mmol/l) and a low battery condition.

It should be noted that the information shown on display 205 is controlled by display driver software for lancing device 11. The display driver software provides display 205 with the ability to scroll a long message flash a message or a portion of a message, or display alternating messages. In addition, the display driver software can provide display 205 with the ability to flash icons. Furthermore, as display 205 is powering up, the display driver software can support a visual check of display 205 wherein the icons and pixels for display 205 are turned on for a brief period to enable the user to confirm the entire display 205 is functioning properly.

Lancing device 11 preferably derives power from a power source (not shown) disposed within interior cavity 29. The power source may be in the form of one or more replaceable AA-type batteries which are removably mounted into an associated battery compartment in interior cavity 29 and which are preferably accessible through pivotable door 37 formed in front surface 21 of base 15. However, it is to be understood that any source of power capable of providing a suitable direct (DC) voltage can be used to provide power to lancing device 11.

As seen most clearly in FIG. 17, user inputs 203 and display 205 are connected to a processing circuit 207 which, in turn, is connected to a microprocessor 209, memory 211, and instrument software 213. Further, data communication device 201 is similarly connected to processing circuit 207 via test strip circuit 215.

Processing circuit 207 is an application specific integrated circuit (ASIC) which enables a test strip is inserted into direct electrical connection with data communication device 201 to communicate with microprocessor 209. For example, processing circuit 207 enables microprocessor 209 to send signals to data communication device 201 to determine the identity of a strip which is disposed into electrical connection therewith (i.e., to determine whether the strip is a calibration strip, a test strip, or the strip-like interface connector for a communication link). Microprocessor 209 may determine the identity of a strip disposed into electrical connection with data communication device 201 by measuring the impedance of said strip or by detecting the location of the electrical contacts on said strip.

Microprocessor 209 is an application specific integrated circuit (ASIC) that functions as the central processing unit for lancing device 11. As such, microprocessor 209 performs the principal calculation and data management tasks for lancing device 11.

Memory 211 is connected to microprocessor 209 and serves to retain data processed by microprocessor 209, said data being available for subsequent retrieval. Types of information that may be stored in memory 211 include measurement delay times, sample incubation times, number of measurements to be taken during an assay, thresholds against which voltage levels can be compared, values of excitation voltage levels applied to a test strip during assay, analyte value conversion factors, fail-safe assay threshold values, and configurations of circuitry of lancing device 11. It should be noted that memory 211 has the capacity to store a multiplicity of assay results. Specifically, each assay result is typically stored into memory 211 as a data bundle referred to herein as "an event". As can be appreciated, memory 211 is preferably of the type which can store in excess of 400 events.

Instrument software 213 is provided for microprocessor 209, software 213 functioning in response to information received at data communication device 201 from a calibration strip. Specifically, instrument software 213 uses the information received from a calibration strip to control the operation of the lancing device 11. Instrument software 213 also controls operations of lancing device 11 that are independent of information introduced or generated at data communications device 201. For example, instrument software 213 enables the user to recall assay results and assay information, can provide various warning, error, and prompting messages, can permit setting of date and time, can control transmission of data to external devices, can monitor power level or battery level or both, and can provide indications to the user if power drops below a specified level.

Test strip circuit 215 connects data communication device 201 to processing circuit 207. In operation, test strip circuit 215 enables data to pass between data communication device 201 and processing circuit 207.

A pair of device circuits 217 are also connected to processing circuit 207. Device circuits 217 can comprise analog, digital, or mixed-signal circuits, application-specific integrated circuits (ASICs), and passive and active electrical components. Device circuits 217 can perform various electrical functions required by lancing device 11. Specifically, device circuits 217 carry instructions from microprocessor 209 to various functional components of lancing device 11 so that these components can perform their intended functions. As one example, device circuits 217 may serve to drive the clock functions for microprocessor 209.

In use, lancing device 11 can be used in the following manner to measure and store analyte test data. Specifically, an analyte test strip is inserted into data communication device 201 so that the metal contacts on the test strip are in direct metal-to-metal contact with associated metal contacts formed on data communication device 201, thereby establishing a communication channel between the test strip and data communication device 201. Having inserted the test strip into data communication device 201, instrument software 213 identifies the item inserted into data communication device 201 as an analyte test strip. At this time, microprocessor 209 executes software which generates a message on display 205 that notifies the user to deposit a sample onto the test strip. When a sample is deposited onto the reaction area of the test strip, the sample reacts with enzymes in the reaction area which, in turn, produces an electrical response in the form of a decaying electrical current. Test strip circuit 215 converts the decaying current from an analog signal to a digital signal and then passes the converted signal to processing circuit 207. The converted signal is then processed by microprocessor 209 to determine the analyte test value that corresponds to the signal Microprocessor 209 then stores the analyte test data as an event in memory 211 and simultaneously registers the analyte test value on display 205 for the patient to read.

The aforementioned analyte testing process can be repeated as desired. As noted briefly above, each test performed is preferably stored into memory 211 as an event, memory 211 being capable of storing a large quantity of events which can be subsequently retrieved and analyzed by a personal computer using sophisticated data management software.

Figure 18:
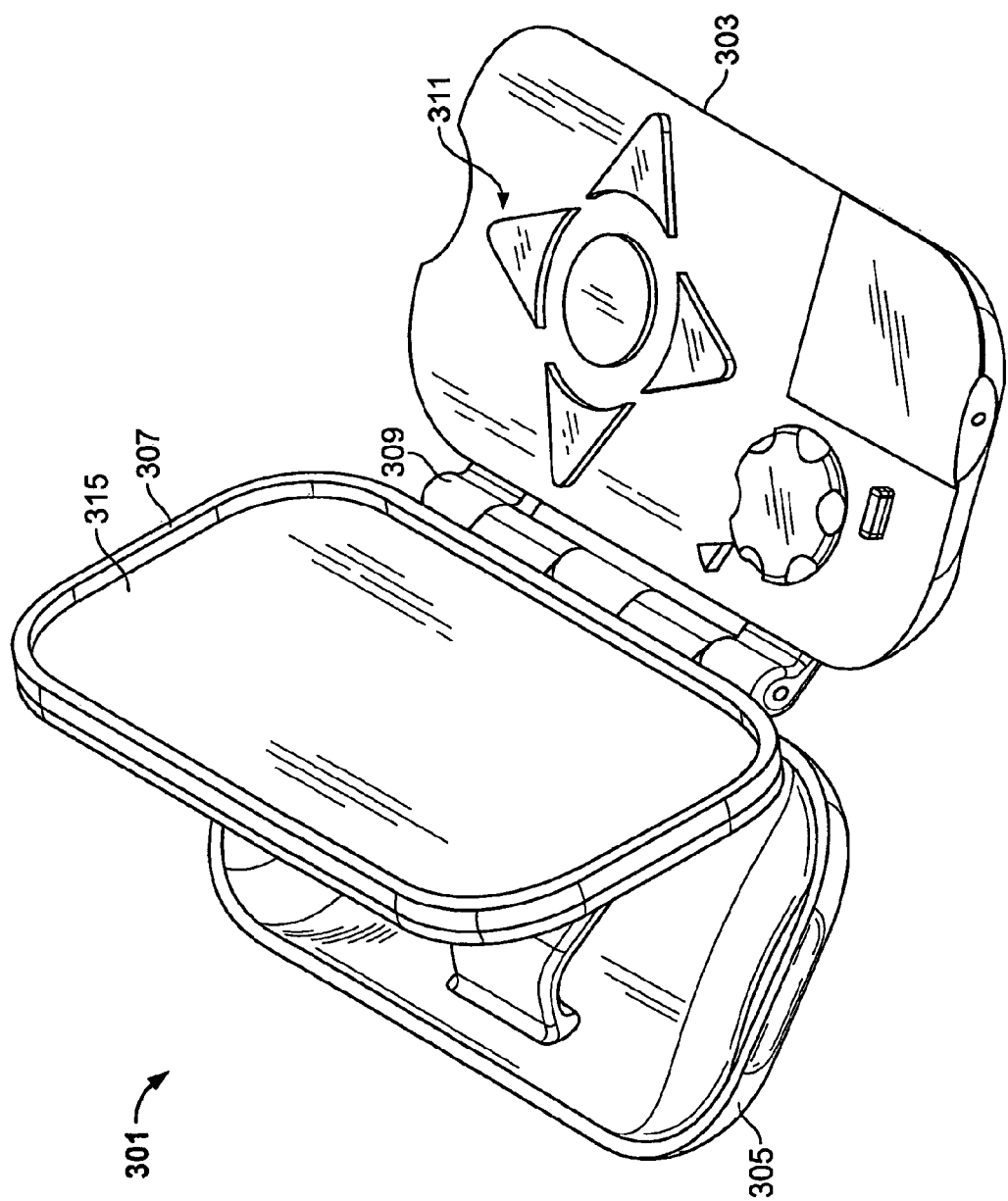
FIG. 18 is a front, right side perspective view of a second embodiment of a lancing device constructed according to the teachings of the present invention.
Figure 19:
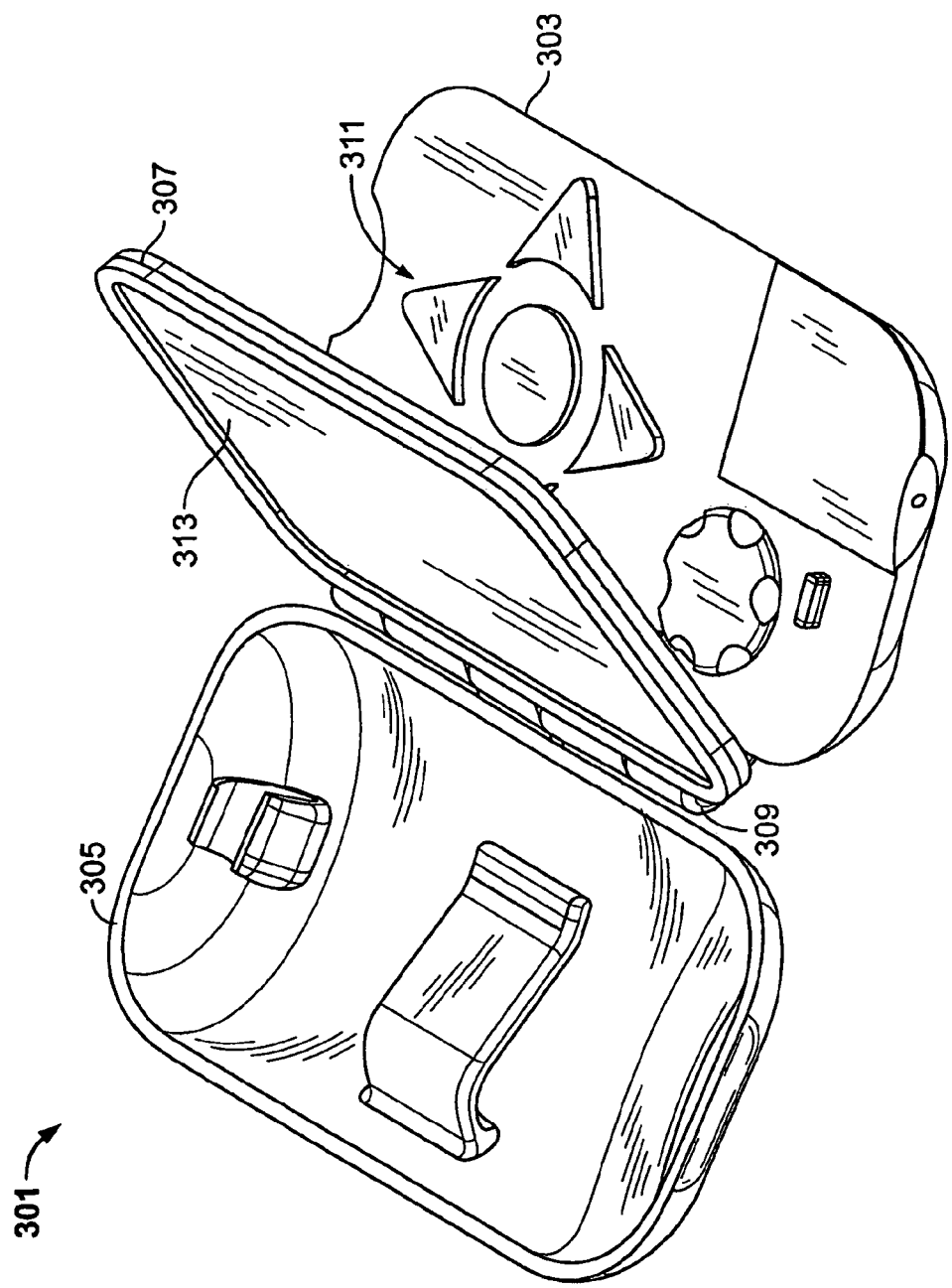
FIG. 19 is a front, left side perspective view of the lancing device shown in FIG. 18.

It should be noted that various modifications to the construction of lancing device 11 could be made without departing from the spirit of the present invention. As an example, referring now to FIGS. 18 and 19, there is shown a second embodiment of a lancing device constructed according to the teachings of the present invention and identified generally by reference numeral 301.

Lancing device 301 differs from lancing device 11 in that lancing device 301 comprises a three component housing whereas lancing device 11 comprises a two component housing. Specifically, lancing device 301 comprises a base 303, a cover 305 and a partition 307 which are pivotally coupled together by a hinge 309.

Base 303 includes the identical internal components found in base 15 of lancing device 11. Base 303 differs principally from base 15 in that base 303 does not include a display. Because base 303 does not include a display, base 303 is capable of supporting a five button interface 311 rather than the two button interface of lancing device 11. As can be appreciated, the increased number of buttons for interface 311 allows for easier user interaction with lancing device 311, which is highly desirable.

Cover 305 is essentially identical in construction with cover 17 of lancing device 11.

Partition 307 is an enlarged rectangular member which is pivotally sandwiched between base 303 and cover 305 by hinge 309. Partition 307 includes a front surface 313 and a rear surface 315.

An enlarged display is preferably provided on substantially the entire portion of rear surface 315 of partition 307. As can be appreciated, such a display would be considerably larger than display 205 of lancing device 11. Furthermore, an enlarged mirror is preferably provided on substantially the entire portion of front surface 313 of partition 307.

The embodiments shown in the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A lancing device comprising:
   (a) a lancet, said lancet having a sharpened tip, and
   (b) a torsion spring coupled to said lancet said torsion spring comprising, (i) a closed inner ring,
(ii) a closed middle ring concentrically configured around said inner ring,
(iii) a closed outer ring concentrically configured around said middle ring,
(iv) a first spring arm connecting said middle ring to said outer ring, and (v) a second spring arm connecting said inner ring to said middle ring,
wherein each of said first and second spring arms is independently transformable between an energized state and a de-energized state.

2. The lancing device of claim 1 wherein said first spring arm extends from said middle ring to said outer ring along an arcuate path.

3. The lancing device of claim 2 wherein said second spring arm extends from said inner ring to said middle ring along an arcuate path.

4. The lancing device of claim 3 wherein said second spring arm extends from said inner ring to said middle ring in the opposite direction in which said first spring arm extends from said middle ring to said outer ring.

5. The lancing device of claim 1 further comprising a housing shaped to define an interior cavity and an opening in communication with said interior cavity.

6. The lancing device of claim 5 wherein said lancet is adapted for movement between a retracted position in which the sharpened tip of said lancet is positioned within the interior cavity of said housing and an extended position in which the sharpened tip of said lancet is positioned outside of the interior cavity of said housing.

7. The lancing device of claim 6 wherein said lancet is disposed in its retracted position when each of said first and second spring arms is in its de-energized state.

8. The lancing device of claim 7 wherein, with said second spring arm maintained in its energized state, transformation of said first spring arm from its energized state to its de-energized state serves to drive said lancet from its retracted position to its extended position.

9. The lancing device of claim 8 wherein, with said first spring arm maintained in its de-energized state, transformation of said second spring arm from its energized state to its de-energized state serves to drive said lancet from its extended position to its retracted position.

10. The lancing device of claim 1 wherein the inner ring of said torsion spring is fixedly coupled to said housing.

11. The lancing device of claim 10 further comprising: (a) a lancet holder for holding said lancet, said lancet holder being fixedly coupled to the outer ring of said torsion spring, and (b) a latch for selectively engaging said lancet holder.

12. The lancing device of claim 11 further comprising: (a) a spring holder fixedly coupled to the middle ring of said torsion spring, and (b) a ratchet for selectively engaging said spring holder.

13. The lancing device of claim 12 further comprising a mechanism fixedly coupled to said spring holder for selectively contacting said latch.

14. A lancing device comprising:
(a) a lancet, said lancet having a sharpened tip, and
(b) a torsion spring coupled to said lancet said torsion spring comprising,
(i) a closed inner ring,
(ii) a closed middle ring concentrically configured around said inner ring,
(iii) a closed outer ring concentrically configured around said middle ring,
(iv) a first spring arm connecting said middle ring to said outer ring, and (v) a second spring arm connecting said inner ring to said middle ring,
wherein, with said second spring arm maintained in its energized state, transformation of said first spring arm from its energized state to its de-energized state serves to drive said lancet from its retracted position to its extended position.

15. The lancing device of claim 14 wherein said first spring arm extends from said middle ring to said outer ring along an arcuate path.

16. The lancing device of claim 15 wherein said second spring arm extends from said inner ring to said middle ring along an arcuate path.

17. The lancing device of claim 16 wherein said second spring arm extends from said inner ring to said middle ring in the opposite direction in which said first spring arm extends from said middle ring to said outer ring.

18. The lancing device of claim 14 wherein each of said first and second spring arms is independently transformable between an energized state and a de-energized state.

19. The lancing device of claim 18 further comprising a housing shaped to define an interior cavity and an opening in communication with said interior cavity.

20. The lancing device of claim 19 wherein said lancet is adapted for movement between a retracted position in which the sharpened tip of said lancet is positioned within the interior cavity of said housing and an extended position in which the sharpened tip of said lancet is positioned outside of the interior cavity of said housing.

21. The lancing device of claim 19 wherein said lancet is disposed in its retracted position when each of said first and second spring arms is in its de-energized state.

22. The lancing device of claim 14 wherein, with said first spring arm maintained in its de-energized state, transformation of said second spring arm from its energized state to its de-energized state serves to drive said lancet from its extended position to its retracted position.

23. The lancing device of claim 14 wherein the inner ring of said torsion spring is fixedly coupled to said housing.

24. The lancing device of claim 23 further comprising: (a) a lancet holder for holding said lancet, said lancet holder being fixedly coupled to the outer ring of said torsion spring, and (b) a latch for selectively engaging said lancet holder.

25. The lancing device of claim 24 further comprising: (a) a spring holder fixedly coupled to the middle ring of said torsion spring, and (b) a ratchet for selectively engaging said spring holder.

26. The lancing device of claim 25 further comprising a mechanism fixedly coupled to said spring holder for selectively contacting said latch.

27. A lancing device comprising:
(a) a lancet, said lancet having a sharpened tip,
(b) a torsion spring coupled to said lancet said torsion spring comprising,
(i) a closed inner ring,
(ii) a closed middle ring concentrically configured around said inner ring,
(iii) a closed outer ring concentrically configured around said middle ring,
(iv) a first spring arm connecting said middle ring to said outer ring, and (v) a second spring arm connecting said inner ring to said middle ring,
(c) a spring holder fixedly coupled to the middle ring of said torsion spring, and
(d) a ratchet for selectively engaging said spring holder.

28. The lancing device of claim 27 wherein said first spring arm extends from said middle ring to said outer ring along an arcuate path.

29. The lancing device of claim 28 wherein said second spring arm extends from said inner ring to said middle ring along an arcuate path.

30. The lancing device of claim 29 wherein said second spring arm extends from said inner ring to said middle ring in the opposite direction in which said first spring arm extends from said middle ring to said outer ring.

31. The lancing device of claim 27 wherein each of said first and second spring arms is independently transformable between an energized state and a de-energized state.

32. The lancing device of claim 31 further comprising a housing shaped to define an interior cavity and an opening in communication with said interior cavity.

33. The lancing device of claim 32 wherein said lancet is adapted for movement between a retracted position in which the sharpened tip of said lancet is positioned within the interior cavity of said housing and an extended position in which the sharpened tip of said lancet is positioned outside of the interior cavity of said housing.

34. The lancing device of claim 33 wherein said lancet is disposed in its retracted position when each of said first and second spring arms is in its de-energized state.

35. The lancing device of claim 34 wherein, with said second spring arm maintained in its energized state, transformation of said first spring arm from its energized state to its de-energized state serves to drive said lancet from its retracted position to its extended position.

36. The lancing device of claim 35 wherein, with said first spring arm maintained in its de-energized state, transformation of said second spring arm from its energized state to its de-energized state serves to drive said lancet from its extended position to its retracted position.

37. The lancing device of claim 27 wherein the inner ring of said torsion spring is fixedly coupled to said housing.

38. The lancing device of claim 37 further comprising: (a) a lancet holder for holding said lancet, said lancet holder being fixedly coupled to the outer ring of said torsion spring, and (b) a latch for selectively engaging said lancet holder.

39. The lancing device of claim 27 further comprising a mechanism fixedly coupled to said spring holder for selectively contacting said latch.

* * * * *